US012414731B2

(12) United States Patent
Ravuna et al.

(10) Patent No.: US 12,414,731 B2
(45) Date of Patent: Sep. 16, 2025

(54) SYSTEM AND METHOD TO DETECT AND IDENTIFY CARDIAC PACE-MAPPING SITES AND PACING MANEUVERS

(71) Applicant: Biosense Webster (Israel) Ltd., Yokneam (IL)

(72) Inventors: Eliyahu Ravuna, Kiryat Ata (IL); Shiran Eliyahu, Yokneam Illit (IL); Shmuel Auerbach, Kerem Maharal (IL); Lior Botzer, Timrat (IL); Elad Nakar, Timrat (IL); Ana Kaufman, Zichron Ya'akov (IL); Jonathan Yarnitsky, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 882 days.

(21) Appl. No.: 17/391,249

(22) Filed: Aug. 2, 2021

(65) Prior Publication Data

US 2022/0039730 A1 Feb. 10, 2022

Related U.S. Application Data

(60) Provisional application No. 63/062,715, filed on Aug. 7, 2020.

(51) Int. Cl.
*G16H 50/20* (2018.01)
*A61B 5/00* (2006.01)
(Continued)

(52) U.S. Cl.
CPC .............. *A61B 5/367* (2021.01); *A61B 5/287* (2021.01); *A61B 5/363* (2021.01); *A61B 5/7246* (2013.01);
(Continued)

(58) Field of Classification Search
USPC ......................................................... 706/16
See application file for complete search history.

(56) References Cited

U.S. PATENT DOCUMENTS

| 5,555,345 A | 9/1996 | Komori et al. |
| 7,907,994 B2 | 3/2011 | Stolarski et al. |
| (Continued) | | |

FOREIGN PATENT DOCUMENTS

WO 2020/142539 A1 7/2020

OTHER PUBLICATIONS

Bhargava, Kartikeya, Pacing Maneuvers: How to differentiate the SVTs?, 2015,(https://www.researchgate.net/publication/k305392562_Pacing_Maneuvers_How_to_differentiate_the_SVTs) (Year: 2015).*
(Continued)

*Primary Examiner* — Austin Hicks
(74) *Attorney, Agent, or Firm* — Volpe Koenig

(57) ABSTRACT

Systems and methods are disclosed for generating a pace-mapping prediction model. Techniques are provided that utilize a training dataset associated with biometrics of patients' hearts, including electrophysiological data associated with cardiac arrhythmia, pace-mapping datasets, and correlation data measuring the degree of correlation between the pace-mapping datasets and the electrophysiological data. Based on the training dataset, the pace-mapping prediction model is trained to predict a degree of correlation between a patient's electrophysiological data and a pace-mapping dataset. Based on the predicted degree of correlation, a cardiac location in the heart of a patient is predicted as the location for the next pace-mapping. Further systems and methods are disclosed for generating a pacing maneuver prediction model. The pacing maneuver prediction model is trained to predict interval measurement based on a pacing maneuver obtained during cardiac pace-mapping.

22 Claims, 14 Drawing Sheets

(51) Int. Cl.
*A61B 5/287* (2021.01)
*A61B 5/363* (2021.01)
*A61B 5/367* (2021.01)
*G16H 50/50* (2018.01)

(52) U.S. Cl.
CPC .......... *A61B 5/7267* (2013.01); *A61B 5/7275* (2013.01); *G16H 50/20* (2018.01); *G16H 50/50* (2018.01)

(56) References Cited

U.S. PATENT DOCUMENTS

2008/0188765 A1    8/2008   Stolarski
2008/0281371 A1*  11/2008   KenKnight ............ A61N 1/365
                                                         607/19
2022/0061732 A1*   3/2022   Krummen ............... A61B 5/341

OTHER PUBLICATIONS

Bharg reference (Year: 2015).*
European Search Report for corresponding EPA No. 21190023.8 dated Jan. 11, 2022.
Zhou Shijie et al., "Automated intraprocedural localization of origin of ventricular activation using patient-specific computed tomographic imaging", Heart Rhythm, vol. 17, No. 4, Oct. 25, 2019, pp. 567-565.
Extended European Search Report issued on Mar. 14, 2025 for European Patent Application No. 24217323.5.
Bhargava, K., "Pacing Maneuvers: How to differentiate the SVTs", (2017).
Extended European Search Report issued on Mar. 14, 2025 for European Patent Application No. 24217328.4.
Japanese Office Action issued on May 20, 2025 for Japanese Patent Application No. 2021-129636.

* cited by examiner

100

200

300

400

INDUCED ECG SIGNALS 510

PACE-MAPPED ECG SIGNALS 520

FIG. 6
600

FIG. 7
700

800

900

RECEIVE COMPLETE PACE MAPS, EACH COMPRISING A CORRELATION MATRIX, EACH ELEMENT OF THE MATRIX CORRESPONDS TO ONE CARDIAC LOCATION AND REPRESENTS A DEGREE OF CORRELATION BETWEEN A PATIENT'S ELECTROPHYSIOLOGICAL DATA AND A PACE-MAPPING DATASET CORRESPONDING TO THE ONE CARDIAC LOCATION
1010

↓

RECEIVE INCOMPLETE PACE MAPS, EACH COMPRISING A DUPLICATE CORRELATION MATRIX OF THAT OF A CORRESPNDING COMPLETE PACE MAP, WHEREIN ONE OR MORE ELEMENTS OF THE MATRIX, SELECTED RANDOMLY, ARE SET TO A PRE-DETERMINED VALUE, INDICATIVE OF AN UNKNOWN VALUE
1020

↓

TRAIN A MODEL TO RECEIVE AN INCOMPLETE PACE MAP AND TO OUTPUT A PREDICTED COMPLETE PACE MAP
1030

SYSTEM AND METHOD TO DETECT AND IDENTIFY CARDIAC PACE-MAPPING SITES AND PACING MANEUVERS

CROSS REFERENCE TO RELATED APPLICATION

This application claims the benefit of U.S. Provisional Patent App. No. 63/062,715, filed Aug. 7, 2020, the disclosure of which is hereby incorporated by reference herein by its entirety.

BACKGROUND

Cardiac arrhythmias such as atrial fibrillation (AF), ventricular fibrillation, ventricular tachycardia (VT), or atrial flutter may cause morbidity and death. Treatments for cardiac conditions such as a cardiac arrhythmia often require obtaining a detailed mapping of the heart's cardiac tissue, chambers, veins, arteries, and/or electrical pathways; such mapping assists with identifying problematic areas of scarred tissue or arrhythmia sources (e.g., electric rotors), as well as healthy areas. For example, as a prerequisite to performing a catheter ablation, the spatial origin of the cardiac arrhythmia must be accurately located in the heart. Localization of the origin of the cardiac arrhythmia in the heart may involve an electrophysiological investigation.

Electrophysiological investigation—namely, electrophysiological (EP) cardiac mapping or cardiac electro-anatomical mapping—provides 3D mapping data. The 3D mapping data may be constructed based on electrical potentials that are measured from signals emitted by a catheter that is introduced into the heart chambers. The 3D mapping data may be based on various modalities, such as local activation time (LAT), an electrical activity, unipolar or bipolar voltage, topology, dominant frequency, or impedance, for example. Thus, data corresponding to various modalities may be captured using a catheter inserted into a patient's body. The captured data may be processed and/or visualized on a display to be viewed by a medical professional or may be stored for later processing and/or visualization.

Myocardial scars are known to be associated with arrhythmic conductive pathways and foci (e.g., reentrant foci) that are responsible for VT. In order to maximize the likelihood of successful catheter ablation, precise localization of a suspected arrhythmogenic foci is necessary. Localization of a suspected arrhythmogenic foci can be achieved through pacing—that is, the action of introducing a signal at a certain location (site) in the ventricles and measuring the corresponding electrical potentials. Hence, pacing at different sites in the ventricles can be used to identify the site that is likely to be the origin of a VT in a patient. A likely origin is expected to be at a site for which the pacing resulted in a measured electrical potential that matches the electrical potential measured from an induced VT, performed in the patient beforehand.

Conventional pace-mapping techniques require that a skilled technician, such as a physician, obtain electrical potential signals (that is, pace-mapping data) from multiple points within the cardiac area of interest, such as a ventricle. Typically, electrical activity associated with a point in the heart is generated by first advancing a catheter (containing an electrical sensor at or near its distal tip) to contact the tissue at that point in the heart, and, then, emitting a signal by the catheter's sensor, generating the electrical activity that is measured and associated with that point. This process is repeated at multiple points in the heart and the data measured at each point are stored in a map (i.e. pace map) that represents the heart's electrical activity at these points. For example, in clinical settings, it is typical to accumulate data at 100 or more sites in the heart to generate a detailed, comprehensive pace map of a heart chamber electrical activity. The pace-mapping data, associated with a site in the heart, are compared with corresponding data, for example, electrophysiological data generated from an induced VT, to determine the degree of correlation, and, thereby, the likelihood that the origin of the induced VT is the same as the paced site in the heart.

Currently, the identification of multiple points of interest in cardiac tissue associated with arrhythmic conductive pathways and foci is difficult and tedious as it requires trial and error by a skilled technician, such as a cardiologist, to find a pacing site that is associated with electrical activity with a high correlation with the electrical activity that is associated with an induced VT. Methods and systems are needed to improve the accuracy and efficiency of identification of sites that are likely to be the origin of cardiac arrhythmia.

SUMMARY

Systems and methods are disclosed in the present disclosure for detecting and identifying cardiac pace-mapping sites and pacing maneuvers.

Aspects disclosed in the present disclosure describe a method for training a pace-mapping prediction model. The method comprises receiving a training dataset associated with patients' hearts. For each patient the training dataset comprises: electrophysiological data associated with a cardiac arrhythmia in the patient; pace-mapping datasets, each dataset is obtained from an electrode when positioned at a cardiac location in the patient's heart; and correlation data, measuring a degree of correlation between each of the pace-mapping datasets and the electrophysiological data. The method also comprises training, based on the training dataset, the pace-mapping prediction model to predict a degree of correlation between electrophysiological data and pace-mapping dataset associated with a new patient.

Aspects disclosed in the present disclosure also describe a system for training a pace-mapping prediction model. The system comprises at least one processor and memory storing instructions. The instructions, when executed by the at least one processor, cause the system to receive a training dataset associated with patients' hearts. For each patient the training dataset comprises: electrophysiological data associated with a cardiac arrhythmia in the patient; pace-mapping datasets, each dataset is obtained from an electrode when positioned at a cardiac location in the patient's heart; and correlation data, measuring the degree of correlation between each of the pace-mapping datasets and the electrophysiological data. The instructions then cause the system to train, based on the training dataset, the pace-mapping prediction model to predict a degree of correlation between electrophysiological data and pace-mapping dataset associated with a new patient.

Further, aspects disclosed in the present disclosure describe a non-transitory computer-readable medium comprising instructions executable by at least one processor to perform a method for training a pace-mapping prediction model. The method comprises receiving a training dataset associated with patients' hearts. For each patient the training dataset comprises: electrophysiological data associated with a cardiac arrhythmia in the patient; pace-mapping datasets, each dataset is obtained from an electrode when positioned at a cardiac location in the patient's heart; and correlation data, measuring the degree of correlation between each of the pace-mapping datasets and the electrophysiological data. The method also comprises training, based on the training dataset, the pace-mapping prediction model to predict a degree of correlation between electrophysiological data and pace-mapping dataset associated with a new patient.

Aspects disclosed in the present disclosure describe a method for training a pacing maneuver prediction model. The method comprises receiving a training dataset associated with patients' hearts. For each patient the training dataset comprises: pacing maneuvers, each associated with pacing locations in the patient's heart; and corresponding interval measurements, each associated with a distance between a last paced pulse and a native beat from a corresponding pacing maneuver. The method also comprises training, based on the training dataset, the pacing maneuver prediction model to predict an interval measurement based on a pacing maneuver associated with a new patient.

Aspects disclosed in the present disclosure also describe a system for training a pacing maneuver prediction model. The system comprises at least one processor and memory storing instructions. The instructions, when executed by the at least one processor, cause the system to receive a training dataset associated with patients' hearts. For each patient the training dataset comprises: pacing maneuvers, each associated with pacing locations in the patient's heart; and corresponding interval measurements, each associated with a distance between a last paced pulse and a native beat from a corresponding pacing maneuver. The instructions also cause the system to train, based on the training dataset, the pacing maneuver prediction model to predict interval measurement based on a pacing maneuver associated with a new patient.

Further, aspects disclosed in the present disclosure describe a non-transitory computer-readable medium comprising instructions executable by at least one processor to perform a method for training a pacing maneuver prediction model. The method comprises receiving a training dataset associated with patients' hearts. For each patient the training dataset comprises: pacing maneuvers, each comprises associated with pacing locations in the patient's heart; and corresponding interval measurements, each associated with a distance between a last paced pulse and a native beat from a corresponding pacing maneuver. The method also comprises training, based on the training dataset, the pacing maneuver prediction model to predict interval measurement based on a pacing maneuver associated with a new patient.

BRIEF DESCRIPTION OF THE DRAWINGS

A more detailed understanding may be had from the following description, given by way of example in conjunction with the accompanying drawings, wherein like reference numerals in the figures indicate like elements, and wherein:

FIG. 6 illustrates an example for training a model to predict a complete pace map from an incomplete pace map, based on which one or more features of the disclosure may be implemented;

FIG. 7 illustrates another example for training a model to predict a complete pace map from an incomplete pace map, based on which one or more features of the disclosure may be implemented;

FIG. 10 is a flow chart of another example method for training a pace-mapping prediction model, based on which one or more features of the disclosure may be implemented;

DETAILED DESCRIPTION

Systems and methods are provided for detecting and identifying the origin of cardiac arrhythmia through pace-mapping and pacing maneuvers. Detection and identification are based on machine learning models, trained to predict sites of likely origin of cardiac arrhythmia and pacing maneuvers.

Figure 1:
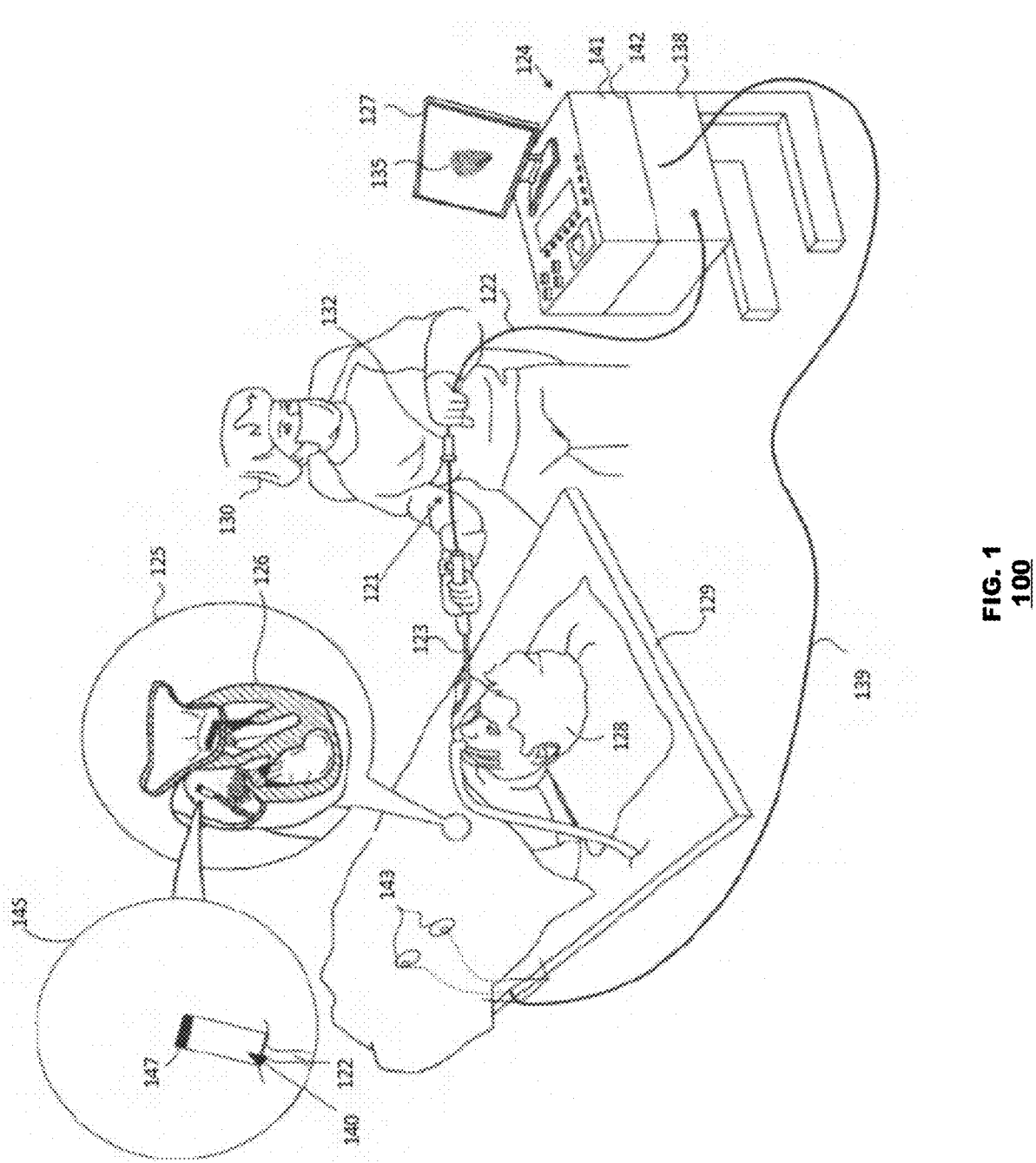
FIG. 1 is a diagram of an example cardiac ablation system, based on which one or more features of the disclosure may be implemented.

FIG. 1 is a diagram of an example cardiac ablation system 100, in which one or more features of the disclosure may be implemented. The system 100 may include a console 124, a display 127, and a catheter 140, operated by a physician 130. The system 100 may be configured to obtain anatomical and electrical measurements, taken from an organ of a patient 128 such as the heart 126, and may be configured to perform a cardiac ablation procedure. The system 100 may be used to collect data for a training dataset used to train a model and may be used to apply the trained model. An example of system 100 is the Carto® system sold by Biosense Webster.

The cardiac ablation system 100 may include a catheter 140, further described with reference to FIG. 3. The catheter 140 may be configured to damage (ablate) tissue areas of an intra-body organ and/or to obtain biometric data including electric signals. The system 100 may include one or more probes 121, having shafts 122 that may be navigated by a physician or a user 130 into a body part, such as the heart 126, of a patient 128 lying on a table 129. The physician 130 may insert a shaft 122 through a sheath 123, while manipulating the distal end of the shafts 122 using a manipulator near the proximal end of the catheter 140 and/or while deflecting from the sheath 123. Inset 145 shows the catheter 140 in an enlarged view, inside a cardiac chamber of the heart 126. As shown, the catheter 140 may be fitted at the distal end of shaft 122. Catheter 140 may be inserted through sheath 123 in a collapsed state and may then be expanded within the heart 126. The catheter 140 may be configured to ablate tissue areas of a cardiac chamber of the heart 126. The catheter 140 may include at least one ablation electrode 147 coupled onto the body of the catheter. For example, an ablation electrode 147 may be configured to provide energy to tissue areas of an intra-body organ such as the heart 126. The energy may be thermal energy and may cause damage to the tissue area starting from the surface of the tissue area and extending into the thickness of the tissue area. Other elements, such as electrodes or transducers, may be part of the catheter and may be configured to ablate as well as to obtain biometric data.

In an aspect, biometric data, obtained by the catheter's elements, may represent information associated with LAT, electrical activity, topology, unipolar or bipolar voltage, dominant frequency, or impedance. LAT may represent a time at which an electrical activity has been measured at a certain location. The LAT may be calculated based on a normalized initial starting point. The electrical activity may be any applicable electrical signal that may be measured based on one or more thresholds. The electrical activity may be sensed and/or may be augmented (e.g., using filters to improve the signal to noise ratios). A topology may represent the physical structure of a body part or a portion of a body part or may correspond to changes in the physical structure between different portions of the body part or between different body parts. A dominant frequency may represent a frequency, or a range of frequencies, that is prevalent in a portion of a body part and may be different in different portions of the same body part. For example, the dominant frequency of a pulmonary vein in the heart may be different from the dominant frequency of the right atrium of the same heart. Impedance may represent resistance at a given area of a body part.

The console 124 of the system 100 may include a processing unit 141 that may comprise a front end and control components (e.g., a computer equipped with a multi-core processor). The console may also include memory 142, e.g., volatile and/or non-volatile memory and communications interface circuitry 138, e.g., for transmitting and receiving signals to and from the catheter 140. The console 124 may be configured to receive biometric data, and, then, to process the biometric data, to store the data for later processing, or to transmit the data to another system via a network. In an aspect, the processing component 141 may be external to the console 124 and may be located, for example, in the catheter 140, in an external device, in a mobile device, in a cloud-based device, or may be a standalone processor. The processing unit 141 may execute software modules programmed to carry out the functions of aspects described herein. The software modules may be downloaded to the processing component 141 over a network or from non-transitory tangible media, such as magnetic, optical, or electronic memory, external or local to the console 124.

The system 100 may be modified to implement aspects disclosed herein. Aspects disclosed herein may be similarly applied using other system components and settings. Additionally, the system 100 may include additional components, such as elements for sensing electrical activity, wired or wireless connectors, processing units, or display devices. The console 124 may include real-time noise reduction circuitry typically configured as a field programmable gate array (FPGA), followed by an analog-to-digital (A/D) ECG (electrocardiograph) or EMG (electromyogram) signal conversion integrated circuit. The output of the A/D ECG or EMG circuit may be processed to perform methods disclosed herein.

In addition to electrical measurements—obtained by a catheter 140 (e.g., ECGs) or other sensors that measure the electrical properties of the heart—in an aspect, the system 100 may also obtain anatomical measurements of the patient's heart. Anatomical measurements may be generated by imaging modalities such as ultrasound, computed tomography (CT), or magnetic resonance imaging (MRI). Hence, the system 100 may obtain biometric data, including anatomical and electrical measurements, and may store the biometric data in the memory 142 of the system 100. The biometric data may be transmitted to the processing unit 141 from the memory 142. Alternatively, or in addition, the biometric data may be transmitted to a server, which may be local or remote to the console 124.

The console 124 may be connected, by a cable 139, to body surface electrodes 143, which may include adhesive skin patches that are affixed to the patient 128. The processing unit 141, in conjunction with a current tracking module, may determine position coordinates of the catheter 140 inside a body part (e.g., the heart 126) of the patient 128. The position coordinates may be based on impedances or electromagnetic fields measured between the body surface electrodes 143 and the electrode 147 or other electromagnetic components of the catheter 140. Additionally, or alternatively, location pads may be attached to the surface of the bed 129.

During a procedure, the processing unit 141 may facilitate the rendering of a body part 135 on a display 127 to be viewed by the physician 130 and may store data representing the body part 135 in the memory 142. In an aspect, the medical professional 130 may be able to manipulate a body part rendering 135 using one or more input devices, such as a touch pad, a mouse, a keyboard, or a gesture recognition apparatus. For example, an input device may be used to change the position of catheter 140 such that the rendering 135 of a body part 126 is updated. In another example, the display 127 may include an input device (e.g., a touchscreen) that may be configured to accept inputs from the medical professional 130, for example, to control the rendering of a body part 135. In an aspect, a display 127 may be located at a remote location such as a separate hospital or in separate healthcare provider networks.

Figure 2:
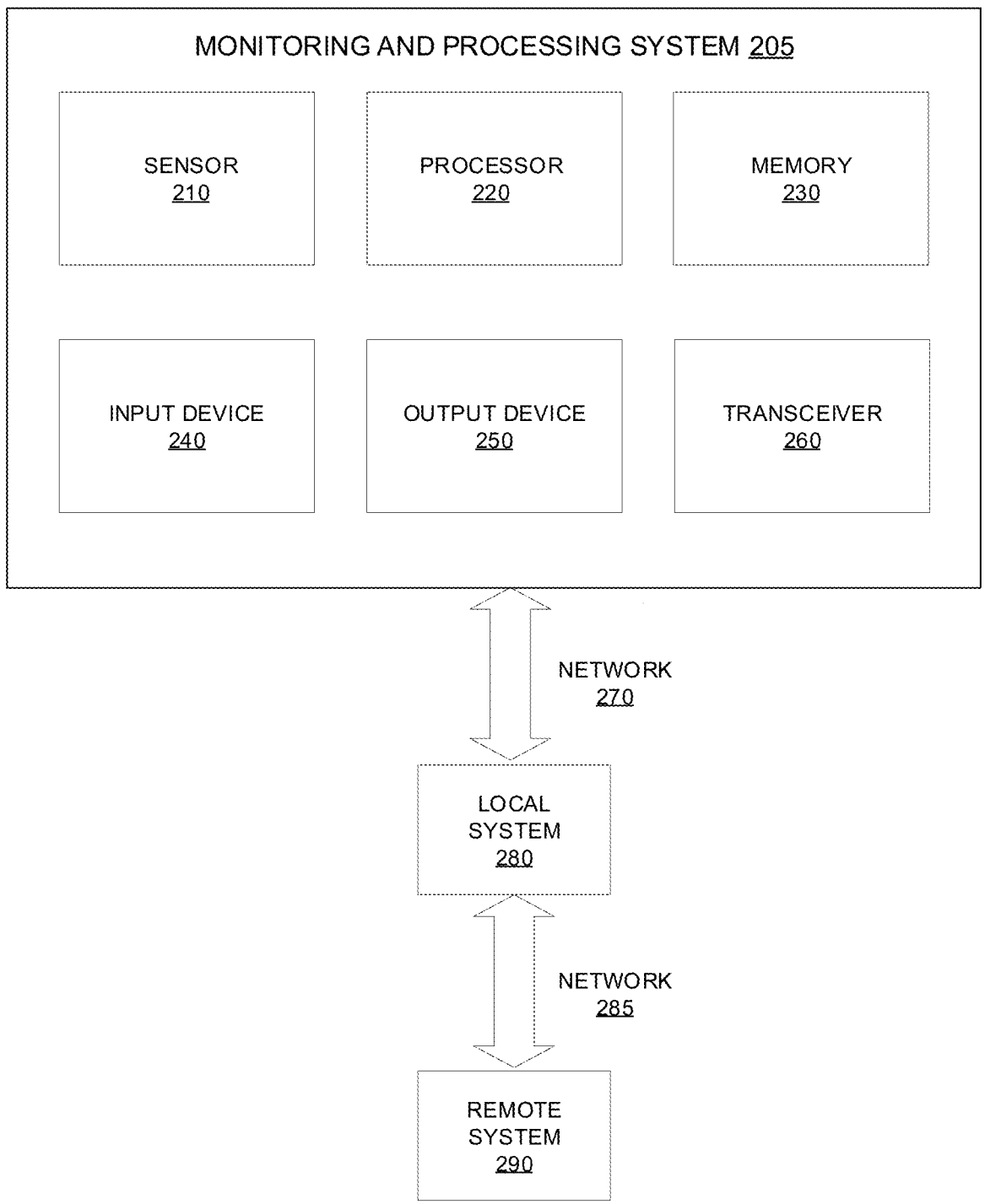
FIG. 2 is a block diagram of an example system, deployable by the example cardiac ablation system of FIG. 1, based on which one or more features of the disclosure may be implemented.

FIG. 2 is a block diagram of an example system 200, deployable by the example cardiac ablation system of FIG. 1, based on which one or more features of the disclosure may be implemented. The system 200 may include a monitoring and processing system 205, a local system 280, and a remote system 290. In an alternative, the monitoring and processing system 205 may represent the console 124 of system 100. The monitoring and processing system 205 may include a patient biometric sensor 210, a processor 220, memory 230, an input device 240, an output device 250, and a transceiver 260, i.e., a transmitter-receiver in communication with a network 270. The system 205 may continually or periodically monitor, store, process, and communicate, via the network 270, various patient biometrics. Examples of patient biometrics include electrical signals (e.g., ECG signals), anatomical images, blood pressure data, blood glucose data, and temperature data. The patient biometrics may be monitored and may be communicated for treatment of various diseases, such as cardiovascular diseases (e.g., arrhythmias, cardiomyopathy, and coronary artery disease) and autoimmune diseases (e.g., type I and type II diabetes).

The monitoring and processing system 205 may be internal to the patient's body—e.g., the system 205 may be subcutaneously implantable, inserted orally or surgically, via a vein or artery, via an endoscopic or a laparoscopic procedure. Alternatively, the system 205 may be external to the patient, e.g., attached to the patient's skin. In an aspect, the system 205 may include both components that are internal to the patient's body and components that are external to the patient's body.

The monitoring and processing system 205, may represent a plurality of monitoring and processing systems 205 that may process biometric data of a patient in parallel and/or in communication with each other or in communication with a server via a network. One or more systems 205 may acquire or receive all or part of a patient's biometric data (e.g., electrical signals, anatomical images, blood pressure, temperature, blood glucose level, or other biometric data). The one or more systems 205 may also acquire or receive additional information associated with the acquired or received patient's biometric data from one or more other systems 205. The additional information may be, for example, diagnosis information and/or information obtained from a device such as a wearable device. Each monitoring and processing system 205 may process data acquired by it and may process data received from another system 205.

The patient biometric sensor 210 may be one or more sensors that may be configured to sense biometric data. For example, the sensor 210 may be an electrode configured to acquire electrical signals (e.g., bioelectrical signals originating in the heart), a temperature sensor, a blood pressure sensor, a blood glucose sensor, a blood oxygen sensor, a pH sensor, an accelerometer, or a microphone. In an aspect, system 205 may be an ECG monitor that measures ECG signals originating in the heart. In such a case, the sensor 210 may be one or more electrodes that may be configured to acquire the ECG signals. The ECG signals may be used for treatment of various cardiovascular diseases. In an aspect, the patient biometric sensor 210 may also include a catheter with one or more electrodes, a probe, a blood pressure cuff, a weight scale, a bracelet (e.g., a smart watch biometric tracker), a glucose monitor, a continuous positive airway pressure (CPAP) machine, or any other device that provides biometric data or other data concerning the patient health.

The transceiver 260 may include a transmitter component and a receiver component. These transmitter component and receiver component may be integrated into a single device or separately implemented. The transceiver may provide connectivity between the system 205 and other systems or servers via a communication network 270. The network 270 may be a wired network, a wireless network or include a combination of wired and/or wireless networks. The network 270 may be a short-range network (e.g., a local area network (LAN) or a personal area network (PAN)). Information may be sent or may be received via the short-range network using various short-range communication protocols such as Bluetooth, Wi-Fi, Zigbee, Z-Wave, near field communications (NFC), ultra-band, Zigbee, or infrared (IR). The network 270 may also be a long-range network (e.g., wide area network (WAN), the internet, or a cellular network). Information may be sent or may be received via the long-range network using various long-range communication protocols such as TCP/IP, HTTP, 3G, 4G/LTE, or 5G/New Radio.

The processor 220 may be configured to process patient's biometric data, obtained by the sensor 210 for example, and store the biometric data and/or the processed biometric data in memory 230. The processor 220 may also be configured to communicate the biometric data across the network 270 via a transmitter of the transceiver 260. Biometric data from one or more other monitoring and processing systems 205 may be received by a receiver of transceiver 260. The processor 220 may employ a machine learning algorithm (e.g., based on a neural network), or, alternatively, a machine learning algorithm may be employed by another processor, e.g., at the local system 280 or the remote system 290. In aspects, the processor 220 may include one or multiple CPUs, one or multiple GPUs, or one or multiple FPGAs. In these aspects, the machine learning algorithm may be executed on one or more of these processing units. Similarly, the processor 220 may include an ASIC dedicated to performing deep learning calculations (such as the Intel® Nervana™ Neural Network Processor) and the machine learning algorithm may be executed on such dedicated ASIC. The processing unit that executes the machine learning algorithm may be located in the medical procedure room or in another location (e.g., another medical facility or a cloud).

The input device 240 of the monitoring and processing system 205 may be used as a user interface. The input device 240 may include, for example, a piezoelectric sensor or a capacitive sensor that is configured to receive user input, such as tapping or touching. Hence, the input device 240 may be configured to implement capacitive coupling in response to tapping or touching a surface of the system 205 by a user. Gesture recognition may be implemented by various capacitive coupling such as resistive capacitive, surface capacitive, projected capacitive, surface acoustic wave, piezoelectric, or infra-red touching. Capacitive sensors may be placed on the surface of the input device 240 so that the tapping or touching of the surface activates the system 205. The processor 220 may be configured to respond selectively to different tapping patterns of the capacitive sensor (e.g., a single tap or a double tap on the input device 240) such that different functions of the system 205 (e.g., acquisition, storing, or transmission of data) may be activated based on the detected pattern. In an aspect, audible feedback may be given to the user from the system 205, e.g., when a gesture is detected and recognized.

In an aspect, the local system 280, that may be in communication with the monitoring and processing system 205 via the network 270, may be configured to act as a gateway to a remote system 290 through another network 285 that may be accessible to the local system 280. The local system 280 may be, for example, a smart phone, smartwatch, tablet, or other portable smart device. Alternatively, the local system 280 may be a stationary or a standalone device. Patient biometric data may be communicated between the local system 280 and the monitoring and processing system 205. In an aspect, the local system 280 may also be configured to display the acquired patient biometric data and associated information.

In an aspect, the remote system 290 may be configured to receive at least part of the monitored patient biometric data and associated information via the network 285, which may be a long-range network. For example, if the local system 280 is a mobile phone, network 285 may be a wireless cellular network, and information may be communicated between the local system 280 and the remote system 290 via a wireless technology standard, such as any of the wireless technologies mentioned above. The remote system 290 may be configured to present received patient biometric data and the associated information to a healthcare professional (e.g., a physician), either visually on a display or aurally through a speaker.

Figure 3:
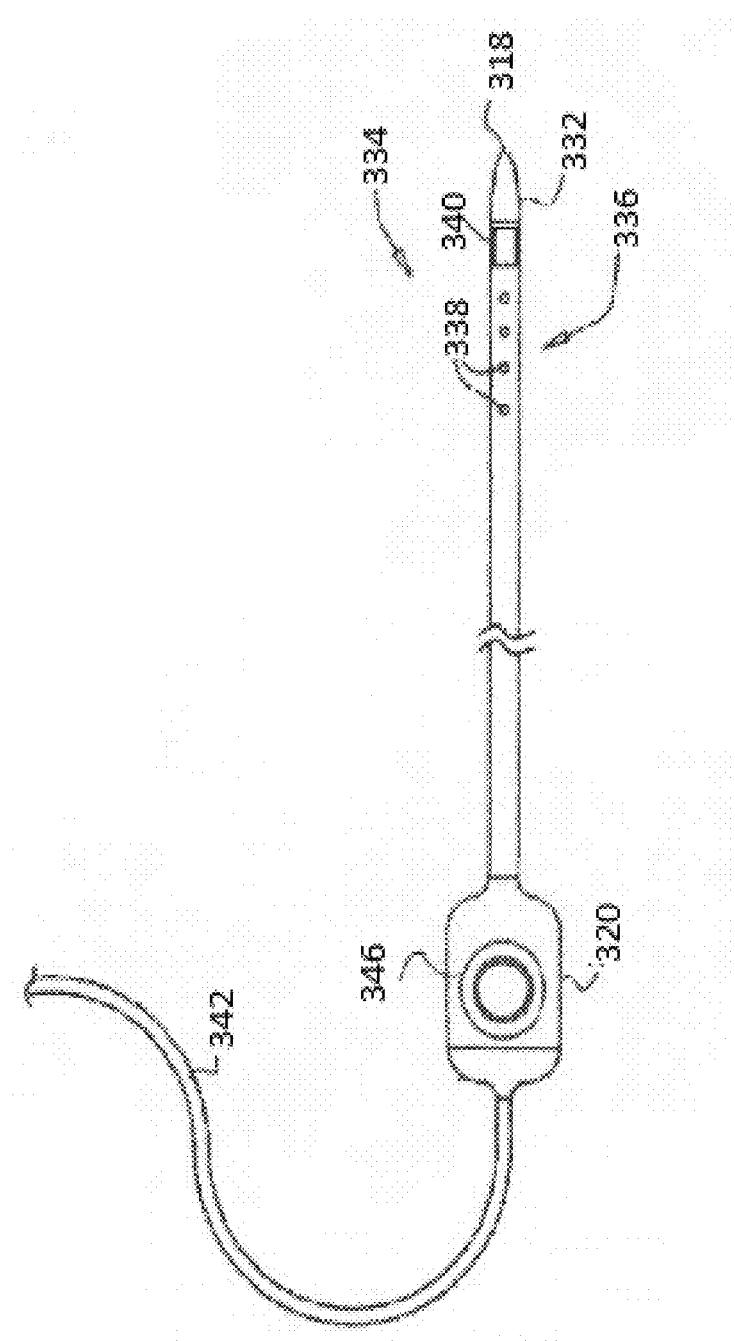
FIG. 3 is an illustration of an example catheter, deployable by the example cardiac ablation system of FIG. 1, based on which one or more features of the disclosure may be implemented.

FIG. 3 is an illustration of an example pace-mapping catheter 300, deployable by the example cardiac ablation system of FIG. 1, based on which one or more features of the disclosure may be implemented. For example, the catheter 300 may be a mapping and therapeutic delivery catheter for insertion into the human body, such as into a chamber of the heart. The catheter 300, shown in FIG. 3, is exemplary; many other types of catheters can be used in accordance with aspects of the present disclosure. An electrode 332 may be positioned at a distal portion 334 for measuring the electrical properties of the heart tissue. The electrode 332 may also be useful for emitting electrical signals into the heart for diagnostic purposes (e.g., for electrical mapping or to induce VT) or for therapeutic purposes (e.g., for ablating defective cardiac tissue). The distal portion 334 of the catheter 300 can further include an array 336 of non-contact electrodes 338 for measuring far field electrical signals in the heart chamber. The array 336 may be a linear array in that the non-contact electrodes 338 are linearly arranged along the longitudinal axis of the distal portion 334. The distal portion 334 may further include at least one position sensor 340 that generates signals used to determine the position and orientation of the distal tip 318 within the body. In an aspect, the position sensor 340 is adjacent to the distal tip 318. There is a fixed positional and orientational relationship among the position sensor 340, the distal tip 318, and the electrode 332. The handle 320 of the catheter 300 may include controls 346 to steer or deflect the distal portion 334, or to orient it as desired.

The position sensor 340 may be configured to transmit, in response to fields that may be produced by system 100 (FIG. 1), position-related electrical signals over a cable 342 running through the catheter 300 to the console 124 (that is, cable 139 shown in FIG. 1). In another alternative, the position sensor 340 in the catheter 300 may transmit signals to the console 124 over a wireless link. The positioning process, e.g., carried out by the processing units 141, 220, may calculate the location and orientation of the distal portion 334 of the catheter 300 based on the signals sent by the position sensor 340. The positioning process may receive, amplify, filter, digitize, and otherwise process signals from the catheter 300. The positioning process can also provide a signal output to a display 127 that may visualize the position of the distal portion 334 and/or the distal tip 318 of the catheter 300 relative to the site chosen for ablation.

Figure 4:
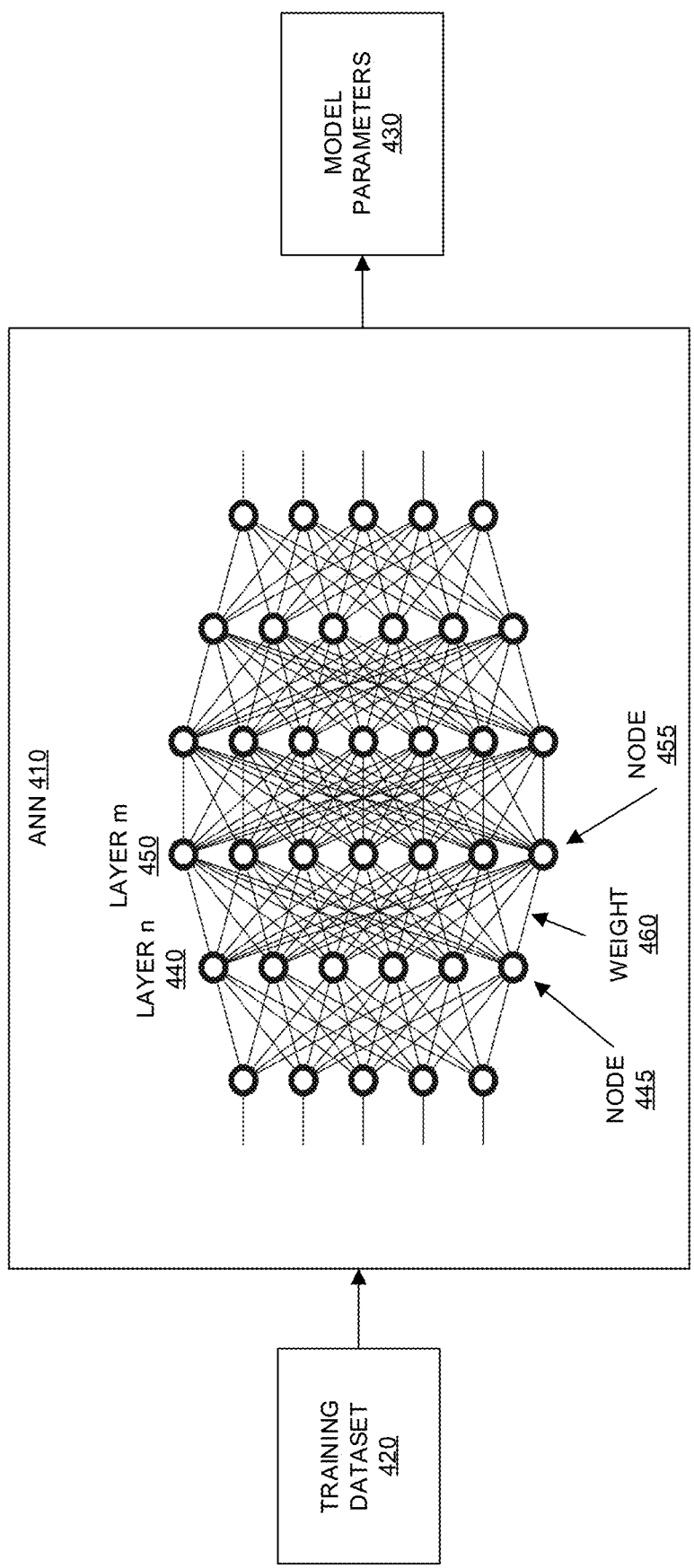
FIG. 4 is a functional block diagram of an example machine learning system, based on which one or more features of the disclosure may be implemented.

FIG. 4 is a functional block diagram of an example machine learning system 400, based on which one or more features of the disclosure may be implemented. Various machine learning systems may be used to train and to apply the pace-mapping prediction model disclosed herein. For example, the machine learning system 400 may be based on artificial neural network (ANN) of various architectures, such as a convolutional neural network (CNN) or a recurrent neural network (RNN), example of which is the long short-term memory (LSTM) network. Generally, neural networks are trained to predict information of interest based on observations. A neural network is trained via a supervised learning process, through which correlations between example pairs (i.e., observations and corresponding information of interest) are learned.

Figure 5B:
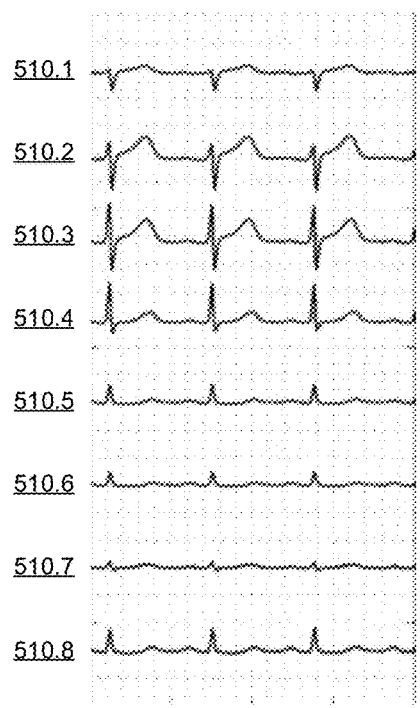
FIGS. 5A-5C illustrate an example pace map (FIG. 5A), recording correlations between induced ECG signals (FIG. 5B) and pace-mapped ECG signals (FIG. 5C), based on which one or more features of the disclosure may be implemented.
Figure 5C:
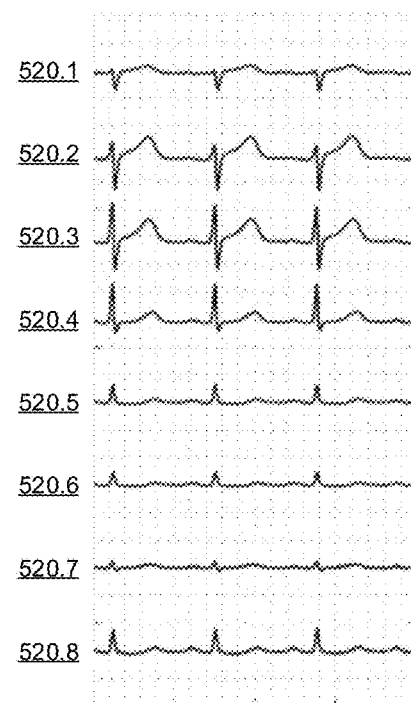
Figure 5A:
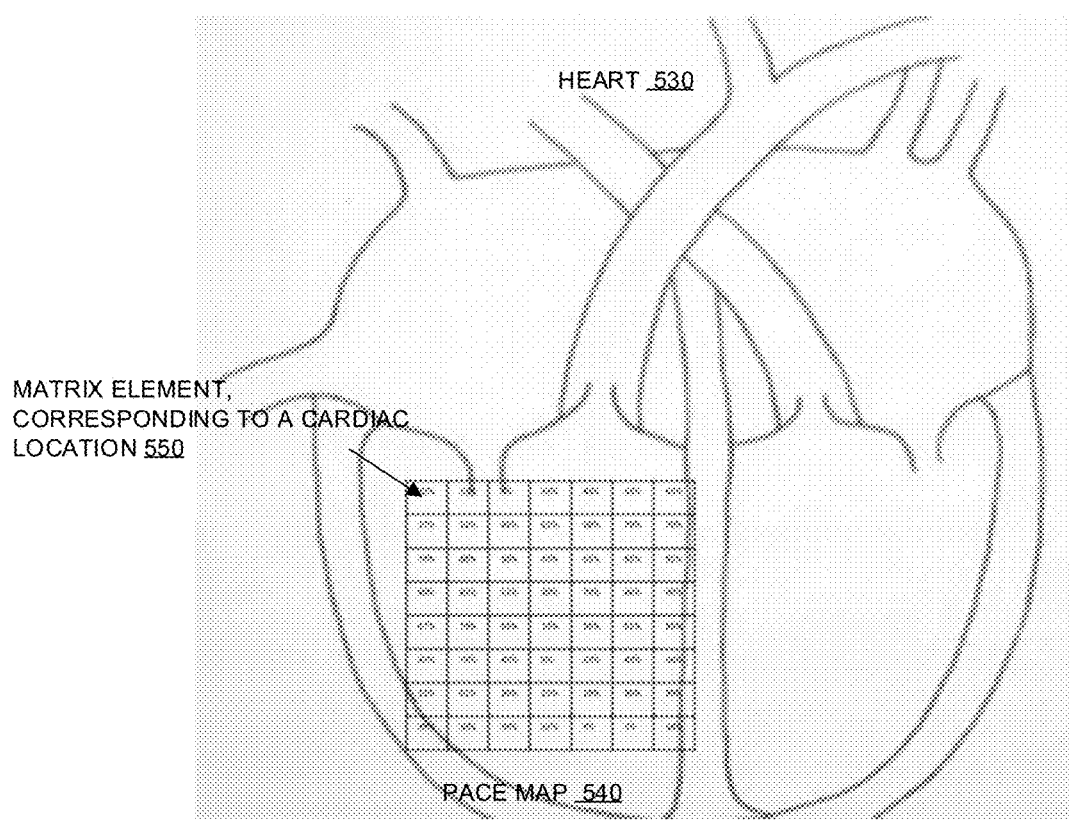

In an aspect, the ANN 410 may be a CNN. A CNN is useful in learning patterns from data provided in a spatiotemporal format, as the pace map 540 that is illustrated in FIG. 5A. Generally, a CNN may employ convolution operations, using kernels, across several layers. Each layer, e.g., layer n 440, in the network may process data from an image at its input and may generate a processed image to be processed by the next layer, e.g., layer m 450. Convolutional kernels that are applied in earlier layers in the network may integrate information from neighboring map elements more efficiently than convolutional kernels that are applied in later layers in the network. Therefore, correlations among image elements that are closely positioned in the map may be better learned in a CNN.

Typically, a neural network 410 comprises nodes ("neurons") that are connected according to a given architecture. For example, in a given architecture, the nodes may be arranged in layers—that is, the output of nodes in one layer, e.g., layer n 440, feed the input of nodes in the next layer connected to it, e.g., layer m 450. A node j 455 of a layer m 450 (i.e., $m_j$) is typically connected to a node i 445 of a layer n 440 (i.e., $n_i$) with a certain strength or a certain weight: $w(m_j, n_i)$ 460. Hence, the weights $\{w(m_j, n_i)\}$ associated with a network's inter-node connections ("synaptic weights") parametrize the neural network model. Training the neural network, then, can be viewed as specializing the network by determining the weights (parameters) of the network, that is, determining the model parameters 430.

The manner in which a neural network 410 processes data may be described as follows. Input data may be fed to nodes in the first layer of a neural network so that each node in the first layer receives a weighted combination of the input data (or a weighted combination of a subset of the input data). Then, each node's inputted weighted combination is translated according to an activation function of the node, resulting in the node's output data. Next, output data from each node in the first layer may be fed to nodes in the second layer of the neural network so that each node in the second layer receives a weighted combination of the outputs of nodes in the first layer (or a weighted combination of the outputs of a subset of the nodes in the first layer). Then, each node's inputted weighted combination is translated according to an activation function of the node, resulting in the node's output data. The output data from nodes of the second layer are then propagated and similarly processed in the other intermediate layers of the network, where the last layer provides the network's output data. Hence, a neural network is typically characterized by the structure of its nodes and these nodes' activation functions. The weights associated with the inter-node connections (the network parameters or model parameters 430) are learned by an iterative training process, e.g., a backpropagation algorithm, according to training parameters (e.g., a learning rate and a cost function) and based on a training dataset 420.

A training dataset 420, based on which a neural network model, 410, may be trained may include pairs of example data, such as observation data (e.g., measurements collected during surgical procedures) and corresponding information of interest to be predicted by the model (e.g., outcomes of the surgical procedures). For example, the temperature data of the heart (observation data) may be collected and may be correlated (by the training process) with outcomes of a heart procedure (information of interest to be predicted). Once the model parameters are determined by the training process, the model can be applied to predict the information of interest based on a new observation. For example, in the case of the heart, based on an input of temperature during a procedure (e.g., between 97.7-100.2 degrees Celsius) the model's output may be a prediction of the outcome of the procedure. Such prediction is based on the correlation between the temperature and the procedure's outcome that was learned by the neural network model based on the training dataset.

Aspects of the present disclosure may train a machine learning model (e.g., ANN 410) and may apply the trained model to detect and/or identify pace-mapping sites. Aspects of the present disclosure may also train a machine learning model and may apply the trained model for pacing maneuvers during cardiac pace-mapping. Algorithms disclosed herein may be applied to train models based on a training dataset, including biometric data measured by various hardware as disclosed herein.

Cardiac arrhythmias, and AF in particular, are common and dangerous medical conditions, especially in an aging population. In patients with normal sinus rhythm, the heart—containing of atrial and ventricular excitatory conduction tissue—is electrically excited to beat in a synchronous and patterned fashion. In patients with cardiac arrhythmias, abnormal regions of cardiac tissues do not follow the synchronous beating cycle associated with normally conductive tissues. Instead, the abnormal regions of cardiac tissue aberrantly conduct to adjacent tissue, thereby disrupting the cardiac cycle into an asynchronous cardiac rhythm. Such an abnormal conduction has been previously known to occur at various regions of the heart, for example, in the region of the sino-atrial (SA) node, along the conduction pathways of the atrioventricular (AV) node and the Bundle of His, or in the cardiac muscle tissue that forms the walls of the ventricular and atrial cardiac chambers.

Cardiac arrhythmias, including atrial arrhythmias, may be of a multiwavelet reentrant type that may be characterized by multiple asynchronous loops of electrical impulses that are scattered about the atrial chamber and are often self-propagating. Alternatively, or in addition to the multiwavelet reentrant type, cardiac arrhythmias may also have a focal origin, such as when an isolated region of tissue in an atrium fires autonomously in a rapid and repetitive fashion. VT is a tachycardia (fast heart rhythm) that originates in one of the ventricles of the heart. This is a potentially life-threatening arrhythmia because it may lead to ventricular fibrillation and sudden death.

One type of arrhythmia, AF, occurs when the normal electrical impulses generated by the sinoatrial node are overwhelmed by disorganized electrical impulses that originate in the atria and pulmonary veins and cause irregular impulses to be conducted to the ventricles. An irregular heartbeat that may result in from such conditions, may last from minutes to weeks, or even years. AF is often a chronic condition that may lead to an increase in the risk of death, often due to strokes. Risk increases with age. Approximately 8% of people over 80 have some degree of AF. AF is often asymptomatic and, generally, is not in itself life-threatening, but it may result in palpitations, weakness, fainting, chest pain and congestive heart failure. Stroke risk increases during AF because blood may pool and form clots in the poorly contracting atria and the left atrial appendage. The first line of treatment for AF is medication that either slow the heart rate or revert the heart rhythm back to normal. Additionally, persons with AF are often given anticoagulants to reduce the risk of stroke. The use of such anticoagulants comes with its own risk of internal bleeding. In some patients, medication is not sufficient, and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation.

A catheter ablation-based treatment may include mapping the electrical properties of the heart tissues, especially the endocardium and the heart volume, and selectively ablating cardiac tissue by the application of energy. Cardiac mapping, for example, creating a map of electrical potentials of the wave propagation along the heart tissue (e.g., a voltage map) or a map of arrival times to various tissue location points (e.g., an LAT map) may be used for detecting local heart tissue dysfunction. Ablations, such as those based on cardiac mapping, can cease or modify the propagation of unwanted electrical signals from one portion of the heart to another.

The ablation process damages the unwanted electrical pathways through the formation of non-conductive lesions. Energy delivery modalities use microwave, laser, and, more commonly, radiofrequency energies to create conduction blocks along the cardiac tissue walls. In a two-step procedure—mapping followed by ablation—activities in various points within the heart are measured (i.e., mapped) some of which are selected to be ablated. Hence, electrical activity at points within the heart may be measured by advancing a catheter (such as the catheter 300 of FIG. 3) into the heart to acquire data at multiple points; then, according to aspects described herein, the acquired data may be utilized to select the endocardial target areas at which ablation is to be performed.

Cardiac ablation and other cardiac electrophysiological procedures have become increasingly complex as clinicians treat challenging conditions such as AF and VT. The treatment of complex arrhythmias can now rely on the use of three-dimensional (3D) mapping systems in order to reconstruct the anatomy of the heart chamber of interest. For example, cardiologists rely upon software such as the Complex Fractionated Atrial Electrograms (CFAE) module of the CARTO® 3 3D mapping system, produced by Biosense Webster, Inc. (Diamond Bar, Calif.), to analyze intracardiac EGM signals and determine the ablation points for treatment of a broad range of cardiac conditions, including atypical atrial flutter and VT. The 3D maps can provide multiple measures of the electrophysiological properties of the tissue that represent the anatomical and functional substrate of these challenging arrhythmias.

In aspects disclosed herein, systems and methods employ machine learning models (e.g., ANN, illustrated in FIG. 4) that may process input data, such as an LAT map, a voltage map, induced ECG signal data, and pace-mapped ECG signal data, in order to determine a cardiac location that is likely to be the origin (foci) of a arrhythmia in a patient.

In conventional pace-mapping systems, such as that disclosed in U.S. Pat. No. 7,907,994, incorporated herein by reference, VT signals are induced in a patient. Pace-mapped signals are then obtained from multiple points within the ventricle, and the obtained pace-mapped signals are compared with the induced signals. Recognition of a high degree of correlation between the induced signals and one or more of the pace-mapped signals may identify arrhythmogenic foci, which may then be ablated. The pace-mapped signals in conventional systems are manually obtained by a physician through trial and error. The physician introduces a pacing catheter (or an electrode) into the heart chamber with which the physician applies electrical stimulation pulses to the myocardium at different locations. The resulting electrical activity (namely, pace-mapped ECG signal data) is recorded. Such an operation referred to herein as pacing or pace-mapping. Typically, many points are paced and only a few are determined to be candidates for ablation. This conventional pace-mapping process is tedious and time-consuming, and can lead to inefficiencies as a result of the trial and error approach to locate pace-mapping sites.

Aspects disclosed herein utilize previously performed pace-mapping cases (e.g., provided by the trial and error process described above) to construct a training dataset 420. The machine learning models disclosed herein, e.g., 410, are trained to output data that may be utilized to predict the next cardiac location to be pace-mapped by the physician. The input data used for training are data from past pace-mapping procedures. For example, the input data may comprise electrophysiological data of a cardiac arrhythmia (e.g., induced ECG signals), pace-mapped data (e.g., pace-mapped ECG signals obtained from a catheter when positioned at a plurality of cardiac locations), an LAT map, or a voltage map. Additionally, for each of the multiple cardiac locations, input data used for training may also include data related to a physician's determination of whether the corresponding pace-mapped data sufficiently correlate with the electrophysiological data of the cardiac arrhythmia to be used as a site for ablation. Once the machine learning model is trained, it may be applied to provide a prediction for a cardiac location for a physician to use as the next pacing site. Such a prediction may provide a higher degree of certainty compared to the trial and error approach described above.

FIG. 5A illustrates an example pace map 540, recording correlations between induced ECG signals 510 (FIG. 5B) and pace-mapped ECG signals 520 (FIG. 5C), based on which one or more features of the disclosure may be implemented. As explained above, ECG signals may be recorded while inducing arrhythmia in a patient. For example, 8-lead induced ECG signals 510.1-510.8 are shown in FIG. 5B. During pacing, multiple pace-mapped ECG signals may be recorded by stimulating the heart 530 at various myocardia locations. For example, 8-lead pace-mapped ECG signals 520.1-520.8 shown in FIG. 5C correspond to a certain myocardia location 550 shown in FIG. 5A. The degree of correlation between the induced ECG signals 510 and the pace-mapped ECG signals 520 is indicative of the likelihood that the induced arrhythmia in the patient was originated from the location in the heart 550 that was stimulated to result in the pace-mapped ECG signals 520.

In an aspect, a pace map 540, denoted by $P_i$, may be computed for each patient i. Each element of the matrix may correspond to a location 550 in the heart at which place the myocardia has been stimulated and may represent a correlation between the induced ECG signals 510 and the pace-mapped ECG signals 520 that correspond to that location 550. In an aspect, a plurality of pace maps, $P_1, P_2, \ldots, P_n$, may be computed; each pace map $P_i$ may be represented by a 3-D matrix, where each matrix element may correspond to a 3D location on the myocardia surface (e.g., right ventricle myocardia) of a patient's heart. Alternatively, the 3D myocardia surface may be projected onto a 2-D planner surface, allowing for a 2D matrix representation of the pace map, $P_i$, such as the 2D matrix 540 that is shown in FIG. 5A. In an aspect, the pace map's values 540 may be percentages, indicating the correlation between induced and paced signals, as explained above. Pace map correlations may be determined using known methodologies, such as those described in U.S. Pat. No. 7,907,994, incorporated by reference herein.

According to aspects disclosed herein, a neural network 410 may be trained to predict a pace map based on a partial map. To that end, each pace map $P_i$ is replicated M times. The replicas are called $P_{i1}, P_{i2}, \ldots, P_{im}$. In each one of the replicas, the correlation values, in one or more randomly selected regions of the matrix, are replaced with a predetermined value, e.g., an out-of-range number such as 999. A replaced value indicates that the correlation in that matrix element is unknown. Then, the neural network is presented with pairs of matrixes, each pair includes a complete map $P_i$ and an incomplete map $P_{im}$—that is, the training dataset is the example pairs $\{P_1, P_1\}, \{P_{12}, P_1\}, \ldots, \{P_{1m}, P_1\}, \{P_{21}, P_2\}, \{P_{22}, P_2\}, \ldots, \{P_{2m}, P_2\}, \ldots, \{P_{n1}, P_n\}, \{P_{n2}, P_n\}, \ldots, \{P_{nm}, P_n\}$. The neural network is then trained to give a predicted $P_i$ for each one of the inputs $P_{i1}, P_{i2}, \ldots, P_{im}$. In this way, the neural network "learns" to predict the complete map (such as pace map 540) from a given incomplete map.

Figure 6:
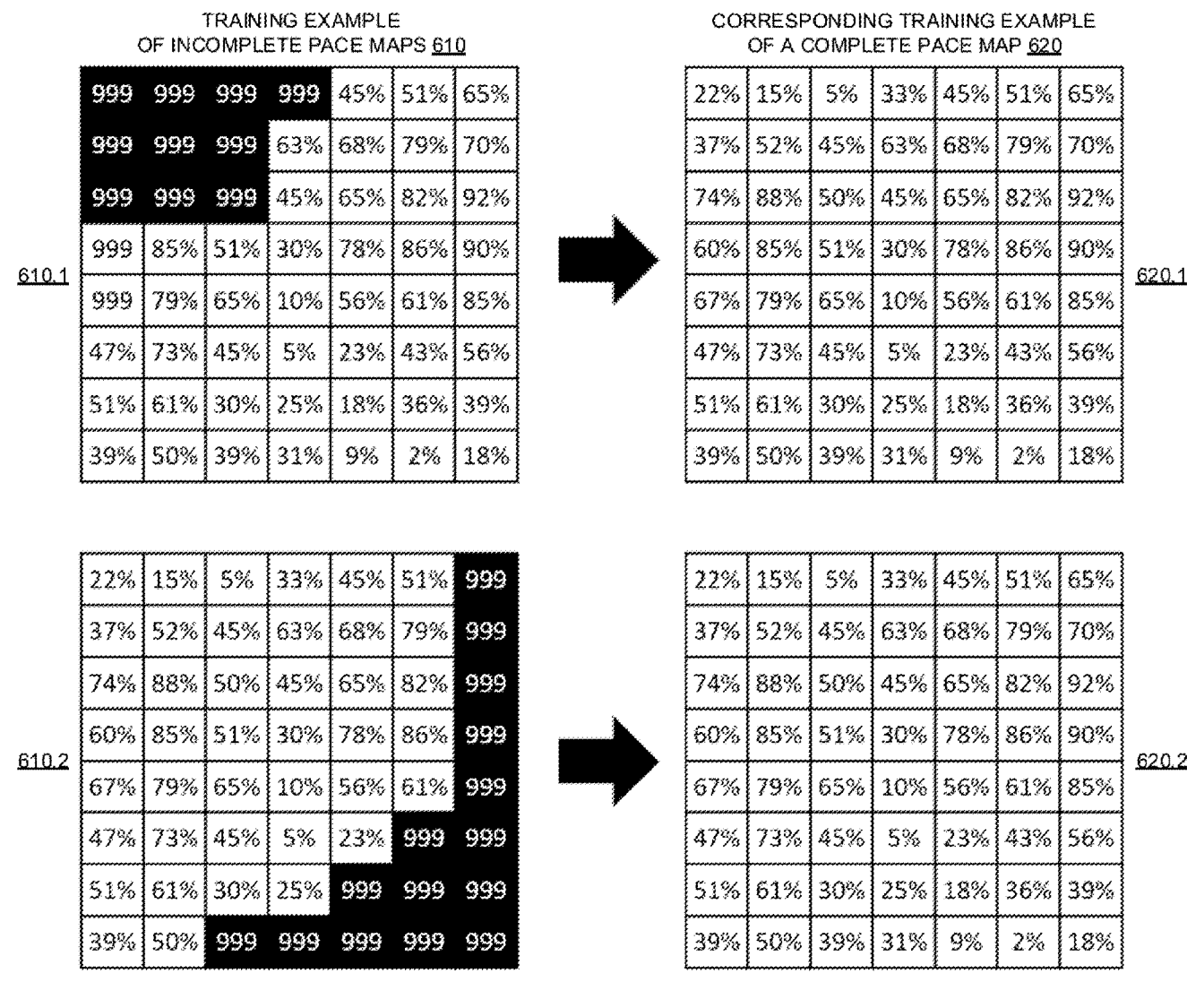

FIG. 6 illustrates an example for training a model 600 to predict a complete pace map from an incomplete pace map, based on which one or more features of the disclosure may be implemented. FIG. 6 illustrates a replica $P_{11}$, 610.1, of $P_1$, 620.1 (e.g., pace map 540), and another replica $P_{12}$, 610.2, of $P_1$, 620.2 (e.g., pace map 540). As explained above, elements of matrix $P_{11}$ and matrix $P_{12}$ were selected randomly and were replaced with an out-of-range number, e.g., 999, to indicate that the values of these selected elements are unknown. For each replica, $P_{11}$ and $P_{12}$, the neural network is trained to give the original map $P_1$. The neural network is optimized so that a cost representing the difference between a replica $P_{1m}$ and its pair $P_1$ is minimized. Setting the unknown correlation value to a number larger than a valid correlation value may contribute to a faster convergence of the neural network. The neural network is trained with as many example pairs 610 and 620 as possible. The trained neural network can be applied to complete unknown regions of a new pace map according to the "experience" it gained from pace maps it was trained on. Hence, the trained neural network may receive at its input a new incomplete pace map, and may provide at its output a predicted complete pace map.

FIG. 7 illustrates another example for training a model 700 to predict a complete pace map from an incomplete pace map, based on which one or more features of the disclosure may be implemented. In an aspect, in addition to creating replicas, 710.1 or 710.3, as described above, a second matrix is created, 710.2 or 710.4, with categorical element values (for example, 0 or 1) that indicate whether the element corresponds to a replaced or to an unknown element in 710.1 or 710.3, respectively. The second matrix may make the neural network converge faster. Thus, in this aspect, a training example 710 may include a replica matrix (e.g., 710.1 or 710.3) and a categorical matrix (e.g., 710.2 or 710.4) and a corresponding pair 720 (e.g., 720.1 or 720.2). As before, the trained neural network may receive at its input a new incomplete pace map, and may provide at its output a predicted complete pace map.

In an aspect, during the pace-mapping process performed by a physician, the system 100, 200 may examine the pace map's correlation values (percentages) that were recorded so far and may treat the rest of the elements in the pace map as unknown (e.g., the system set the unknown elements to out of range values). Then, the system 100, 200 may feed the incomplete pace map (and optionally a corresponding categorical map, as described with reference to FIG. 7) to the neural network 410, as an input. The neural network, which was already trained with numerous maps from its training dataset as explained above, may predict the correlation values (percentages) in the unknown regions. Having a predicted pace map that is fully populated with correlation values, the system 100, 200, may now suggest to the physician a direction or a region in the heart to perform the next map-pacing. The system's 100, 200 recommended direction or region may lead to a location with the highest colleration. The system's recommendation may be indicated by a visual or auditory indication that points to the recommended direction or region. For example, the visual indication may be represented by an arrow, a star, a pin, or any similar visual indication and may be overlayed on the image of the heart 530 presented on the system's display.

In an aspect, instead of indicating the direction the physician should try next as a pacing site, the system may monitor the direction the physician is moving the catheter in, and may evaluate how successful that direction could end up being. Based on that evaluation, the system may provide a success indication as a percentage, a color (e.g., as green-yellow-red traffic lights), brightness, or a sound.

Figure 8:
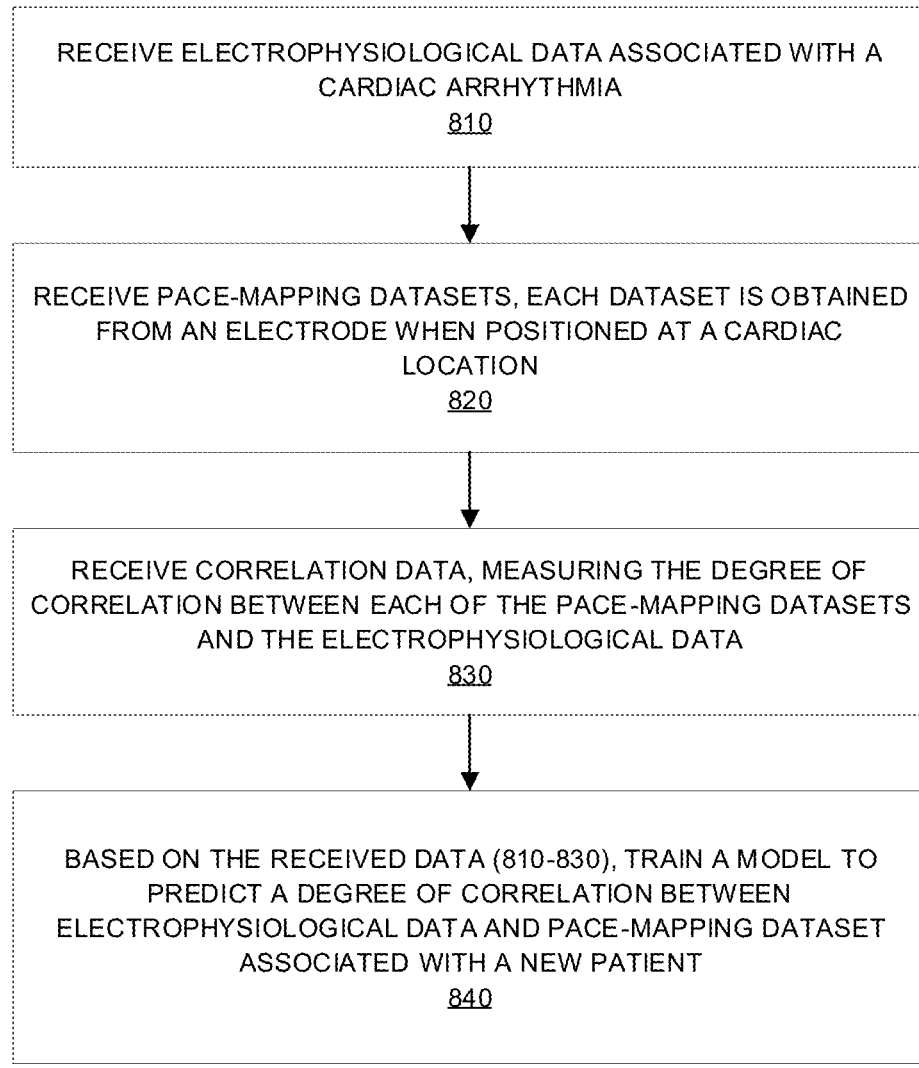
FIG. 8 is a flow chart of an example method for training a pace-mapping prediction model, based on which one or more features of the disclosure may be implemented.

FIG. 8 is a flow chart of an example method 800 for training a pace-mapping prediction model, based on which one or more features of the disclosure may be implemented. The pace mapping model may be based on a neural network, as described in reference to FIG. 4. The method 800 may receive a training dataset based on which the pace-mapping model is trained; the training dataset may include data associated with pace-mapping procedures performed on patients in the past. Thus, for each such patient, the method 800 may receive, in step 810, electrophysiological data associated with a cardiac arrhythmia the patient endured. In step 820, the method 800 may receive pace-mapping datasets. Each dataset is obtained from an electrode (or a catheter) when positioned at a cardiac location in the patient's heart. The method 800 also may receive, in step 830, correlation data that measure the degree of correlation between each of the pace-mapping datasets and the electrophysiological data. Then, the training of the pace-mapping prediction model takes place, in step 840, based on the received training dataset. The pace-mapping prediction model is trained to predict a degree of correlation between electrophysiological data and a pace-mapping dataset of a new patient at a pace-mapping site.

Figure 9:
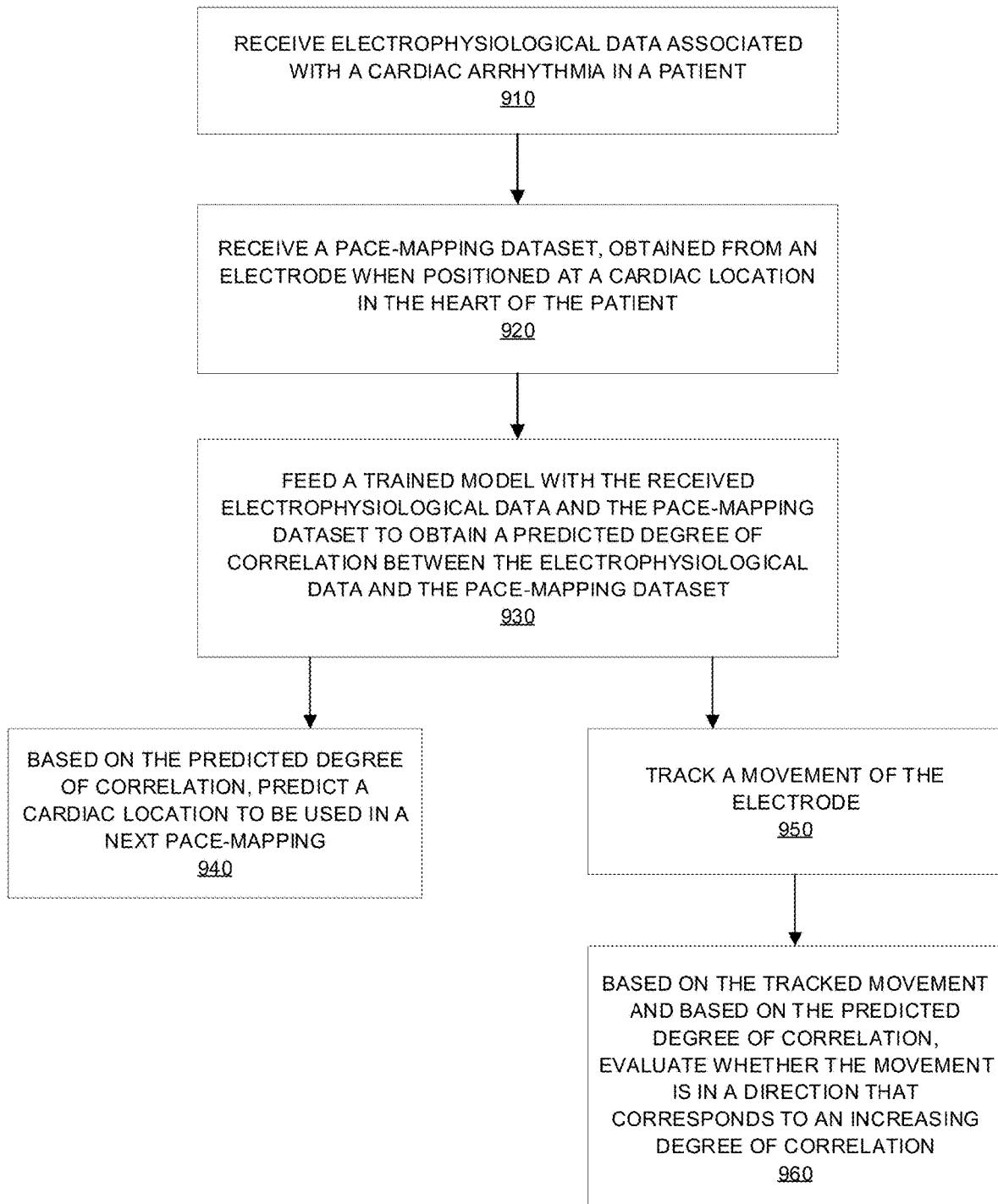
FIG. 9 is a flow chart of an example method for applying the trained model of FIG. 8, based on which one or more features of the disclosure may be implemented.

FIG. 9 is a flow chart of an example method 900 for applying a pace-mapping prediction model, based on which one or more features of the disclosure may be implemented. A trained pace-mapping prediction model, as described with reference to FIG. 8, for example, may be applied to a new patient under care during a pace-mapping procedure. The method 900 may receive as an input electrophysiological data associated with a cardiac arrhythmia that the patient under care has endured, in step 910. Additionally, the method 900 may receive as input a pace-mapping dataset, obtained from an electrode when positioned at a cardiac location in the heart of the patient, in step 920. Then, the method 900 may feed the trained pace-mapping prediction model with the received input data, in step 930, to obtain a predicted degree of correlation between the electrophysiological data and the pace-mapping dataset. The predicted degree of correlation may be used to guide the physician performing the procedure in his search for a pace-mapping site that is likely to be the origin of the cardiac arrhythmia in the patient. In an aspect, the method 900, may predict, in step 940, based on the predicted degree of correlation, a cardiac location in the heart of the patient to be used as the next pace-mapping during the procedure. In another aspect, the method 900, in step 950, may track a movement of the electrode used in the procedure. Then, in step 960, based on the tracked movement and based on the predicted degree of correlation, the method 900 may evaluate whether the movement is in a direction that corresponds to an increasing degree of correlation. In both aspects (the aspect of step 940 and the aspect of steps 950 and 960), the method 900 may utilize multiple predicted values of degree of correlation, corresponding to multiple cardiac locations, by carrying out steps 910-930 multiple times.

FIG. 10 is a flow chart of another example method 1000 for training a pace-mapping prediction model, based on which one or more features of the disclosure may be implemented. The pace mapping model may be based on a neural network, as described in reference to FIG. 4. The method 1000 may receive a training dataset based on which the pace-mapping model is trained. The training dataset may include data of pace map pairs associated with pace-mapping procedures performed on patients in the past. Thus, for each such patient, the method 1000 may receive multiple pace map pairs, each pair includes a complete pace map, and an incomplete pace map (e.g., pair 610.1 and 620.1 or pair 610.2 and 620.2). Accordingly, in step 1010, the method 1000 may receive complete pace maps that each may comprise a correlation matrix. Each element of the matrix may correspond to one cardiac location in the patient's heart and may represent a degree of correlation between a pace-mapping dataset (corresponding to that one cardiac location) and the patient's electrophysiological data. In step 1020, the method 1000 may receive incomplete pace maps that each comprises a duplicate correlation matrix of that of a corresponding complete pace map, wherein one or more elements of the duplicate correlation matrix, selected randomly, are set to a pre-determined value, indicative of an unknown value. In an aspect, for each pair of the pairs of a complete pace map and an incomplete pace map (e.g., pair 710.1 and 720.1 or pair 710.3 and 720.2), a categorical matrix associated with the incomplete pace map in the pair (e.g., 710.2 associated with 710.1 or 710.4 associated with 710.3) may also be received in step 1020. Each element value of the categorical matrix may indicate whether a corresponding element value in the associated incomplete pace map is set to the pre-determined value. Then, in step 1030, the method 1000 may train the pace-mapping prediction model to receive an incomplete pace map of a new patient, containing known and unknown correlation matrix elements, and to provide a predicted complete pace map, containing predictions of the unknown correlation matrix elements.

Figure 11:
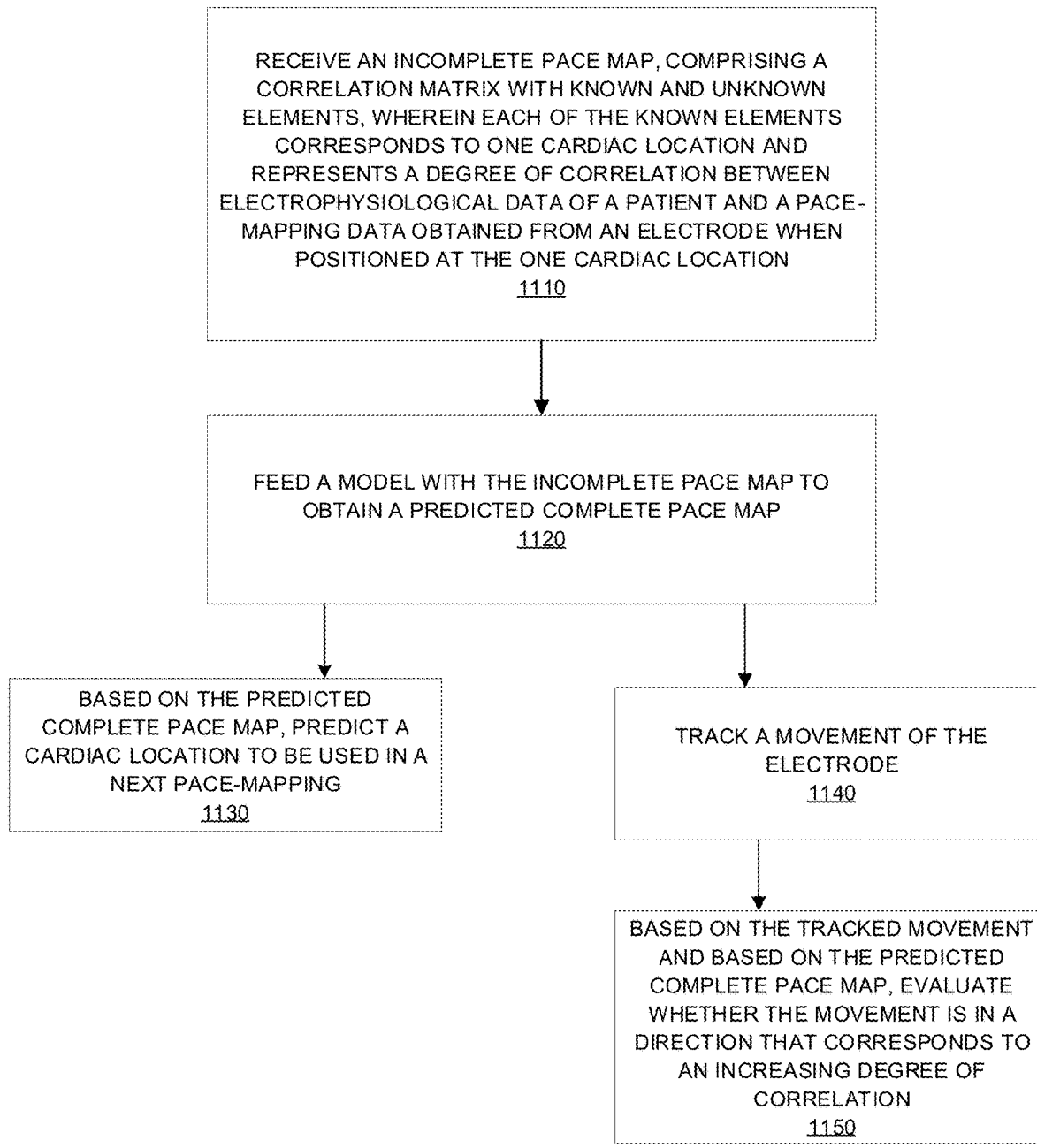
FIG. 11 is a flow chart of an example method for applying the trained model of FIG. 10, based on which one or more features of the disclosure may be implemented.

FIG. 11 is a flow chart of another example method 1100 for applying a pace-mapping prediction model, based on which one or more features of the disclosure may be implemented. A trained pace-mapping prediction model, as described with reference to FIG. 10, for example, may be applied to a patient under care during a pace-mapping procedure. The method 1100, in step 1110, may receive an incomplete pace map, generated during the procedure. The incomplete pace map may comprise a correlation matrix with known and unknown elements. Each of the known elements of the matrix may correspond to one cardiac location in the heart of the new patient and may represent a degree of correlation between the new patient's electrophysiological data and pace-mapping data obtained from an electrode when positioned at the one cardiac location in the heart of the new patient. Then, in step 1120, the method 1100, may feed the pace-mapping prediction model with the new incomplete pace map to obtain a new predicted complete pace map, containing predictions of the unknown elements. The new predicted pace map may be used to guide the physician, performing the procedure, in his search for a pace-mapping site that is likely to be the origin of the cardiac arrhythmia in the patient. In an aspect, method 1100, in step

1130, may predict, based on the new predicted complete pace map, a cardiac location in the heart of the patient to be used as the next p ace-mapping. In another aspect, method 1100, in step 1140, may track a movement of the electrode. Then, in step 1150, the method 1100 may evaluate, based on the tracked movement and based on the new predicted complete pace map, whether the movement is in a direction that corresponds to an increasing degree of correlation.

The electrophysiological data associated with a cardiac arrhythmia endured by a patient (e.g., as mentioned with respect to methods 800, 900, 1000, and 1100) may be induced. For example, the patient may be experiencing VT that is induced by arrhythmogenic drugs, such as Isoproterenol, or by undergoing strenuous activity.

In an aspect, training and applying the machine learning model, as described in reference to FIGS. 4-11, may be performed by the systems described herein, 100 (FIG. 1) or 200 (FIG. 2), also representing the CARTO® 3 3D mapping system, in real-time, on a server at the facility where the cardiac procedure is taking place, such as a hospital or medical facility, or at a remote location, such as in the cloud or at a training center. In an aspect, vendors of the systems, 100 (FIG. 1) or 200 (FIG. 2), may deliver such systems with a pre-trained pace-mapping prediction model. Hospitals may continue to train the system (e.g., to update the pace-mapping prediction model based on augmented or new training datasets). In an aspect, a single pace-mapping prediction model may be maintained for all hospitals, or for a group of hospitals, or every hospital may maintain its own pace-mapping prediction model.

In an aspect of the present application, a machine learning model is utilized to identify sequences of paced pulses in a pacing procedure workflow and automatically measure an interval between the last paced pulse (in a pacing sequence) and the first native beat following the last paced pulse. Such interval measurement may be obtained from a time or a voltage caliper associated with particular ECG signal.

Some electrophysiological procedures require pacing maneuvers for different arrhythmias (such as AF or VT) in which a chain of paced pulses may be generated. The pacing may be generated at one or more cardiac locations and may be measured at one or more cardiac locations and on body surface electrodes. The chain of paced pulses may be generated in equal time distances or may be generated in varying time distances. The system's operator may then open a time or a voltage caliper associated with a particular ECG signal and may measure the distance from the last paced pulse to the first native beat. A pacing maneuver may be useful in characterizing the cardiac tissue, deducing the presence of a short pathway, and identifying the location of a reentrant circuit.

Figure 12:
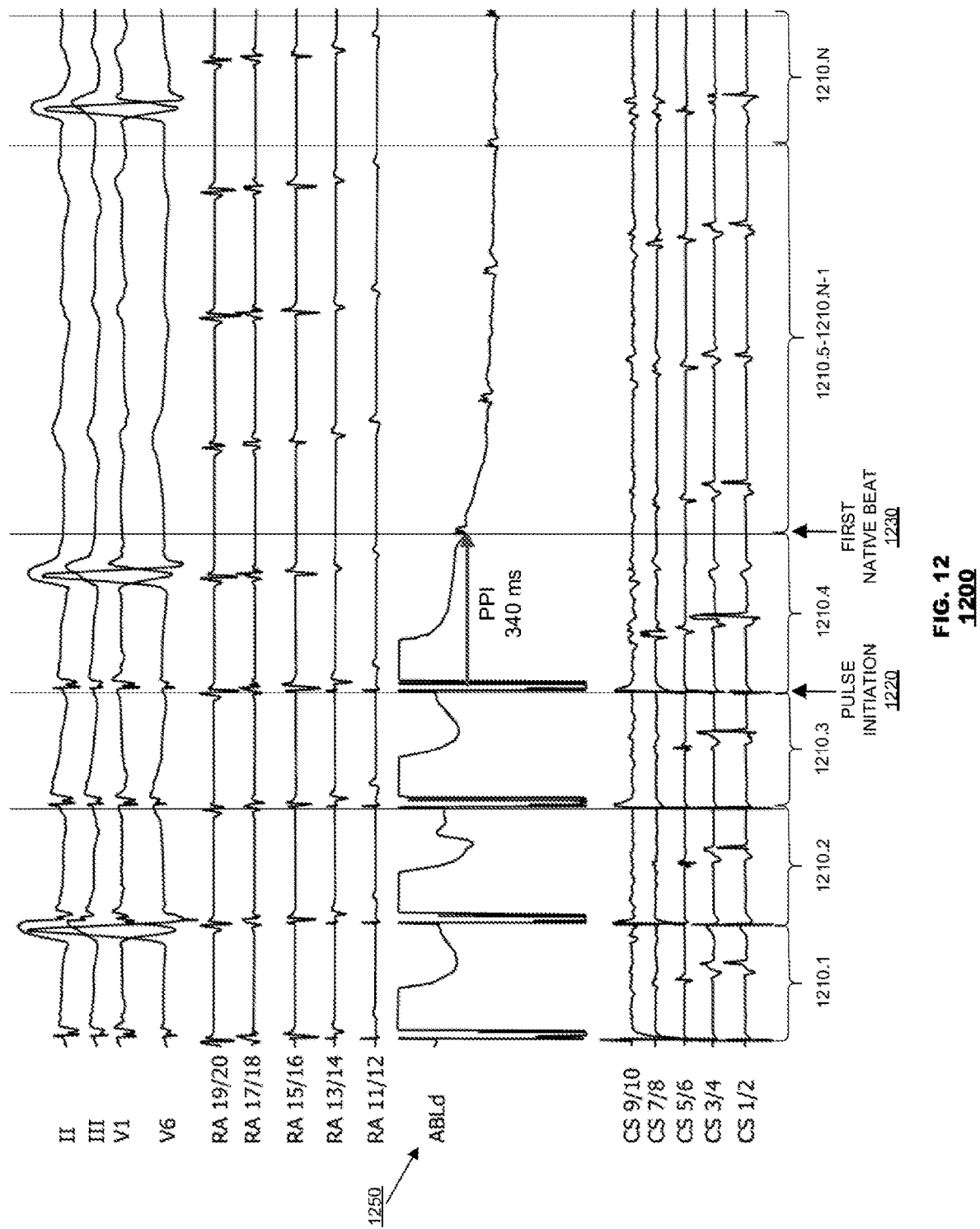
FIG. 12 illustrates an example ECG tracing of a pacing maneuver and time caliper measurements manually obtained by a physician, based on which one or more features of the disclosure may be implemented.

FIG. 12 illustrates an example ECG tracing 1200 of a pacing maneuver and time caliper measurements manually obtained by a physician, based on which one or more features of the disclosure may be implemented. For example, with respect to the ablation catheter, ABLd 1250, a pacing maneuver may comprise a pacing sequence including pulses, each pulse has a time duration associated with it, e.g., 1210.1-1210.4. For example, the last pulse has a 340 milliseconds (ms) duration time 1210.4. A pacing maneuver may also comprise native pulses having time durations associated with them 1210.5-1210.N. A post-pacing interval (PPI) may be defined as the interval 1210.4 that extends from the initiation time of the last pulse 1220 to the time of a first native beat 1230 (henceforth a next native beat). Both the pacing sequence and the native beats may be associated with different cardiac locations and may have different durations, e.g., 1210.1-1210.N.

In an aspect, a machine learning algorithm may be applied to detect, based on a pacing maneuver, interval measurements (of time calipers and/or voltage calipers) that may be accepted, rejected, or modified by a physician. To that end, a machine learning model is trained based on a training dataset, including pacing maneuvers and corresponding interval measurements, manually obtained from a physician. In an aspect, the pacing maneuvers and the corresponding interval measurements of the training dataset are associated with different cardiac locations and having different durations. During the training of the neural network (training phase) and during the application of the trained neural network (inference phase), interval measurements may include the start and the end of a period of a time (or a voltage), and may be represented by: 1) the post pacing interval (time between last pacing spike to the first native beat), e.g., 1210.4; 2) the pacing train properties (regular and irregular time intervals), e.g., 1210.1; 3) the tachycardia cycle length; 4) similar measurements on the Coronary Sinus catheter electrodes; 5) similar measurements on other catheters' electrodes; and 6) a combination thereof.

Figure 13A:
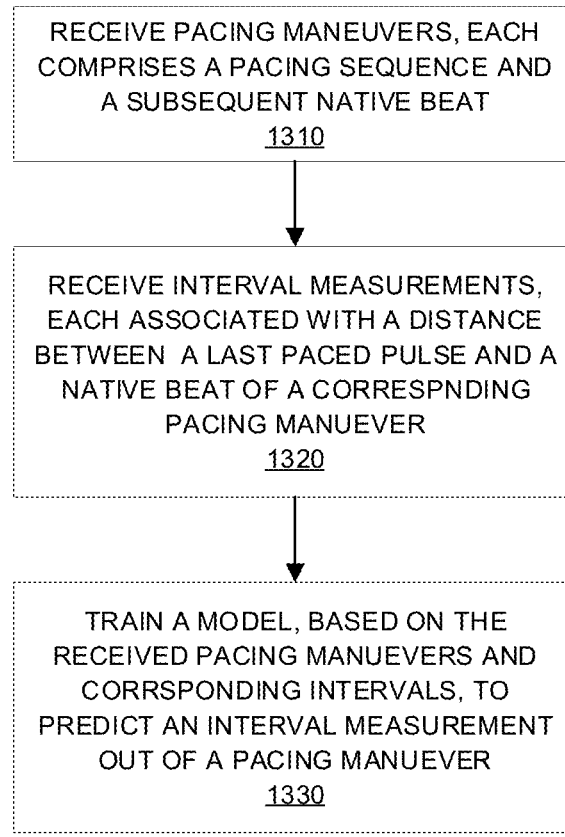
FIGS. 13A-13B illustrate an example flow diagram depicting a training method (FIG. 13A) of a machine learning model and the machine learning model application (FIG. 13B), based on which one or more features of the disclosure may be implemented.
Figure 13B:
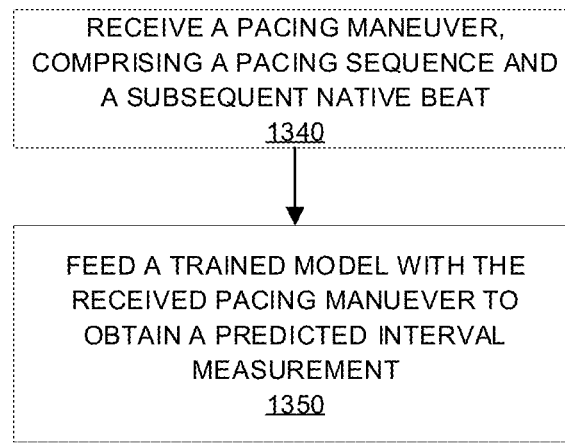

FIGS. 13A-13B illustrate an example flow diagram depicting a training method (FIG. 13A) of a machine learning model and the machine learning model application (FIG. 13B), based on which one or more features of the disclosure may be implemented. Steps 1310-1330 describe the training phase of the machine learning algorithm. Accordingly, in step 1310, pacing maneuvers are received, each pacing maneuver may comprise a pacing sequence and a subsequent native beat associated with cardiac locations. In step 1320, interval measurements, each corresponds to a pacing maneuver, are received. Each received interval measurement 1210.4 may be associated with a distance between the last paced pulse and a next native beat. Then, in step 1330, a machine learning model may be trained based on the received pacing maneuvers 1310 and the corresponding received interval measurements 1320 to predict an interval measurement when presented with a new pacing maneuver. Thus, in an aspect, the machine learning model may be trained based on example pairs of training data—each example pair may include a pacing maneuver (including a pacing sequence and a subsequent native beat) and a corresponding interval measurement. For example, a training pair may include a sequence of 300 ms, 290 ms, 280 ms, and 270 ms, and a corresponding interval measurement (e.g., a time caliper) that measures the distance between the last paced pulse 1220 and the next native beat 1230—e.g., the distance measured from ±10 ms around the last paced pulse 1220 to ±10 ms around the next native beat 1230. The interval measurements may be determined manually by a physician based on respective pacing maneuvers. Thus, the machine learning model learns, for example, the physician's preference to adjust the caliper on the last paced pulse or on the mapping annotation at interval steps of ±10 ms.

Once the machine learning model is trained, as described with reference to FIG. 13A, it may be applied in an inference phase as shown in FIG. 13B. Accordingly, is step 1340, the machine learning model may receive as an input a pacing maneuver that may comprise a pacing sequence and a subsequent native beat. Based on the received pacing maneuver, as trained, the model may output, in step 1350, a prediction for an interval measurement. For example, if the machine learning model receives a sequence of 301 ms, 289 ms, 282 ms, and 269 ms, the machine learning model may predict an interval measurement (a caliper interval) associated with the distance 1210.4 between the last paced pulse and a next native beat. A physician may optionally accept, deny, or modify the predicted caliper interval. For example, if accepted by the physician, the predicted caliper interval may be stored in and/or may be used to update an EP cardiac map generated by the system 100 (FIG. 1) or 200 (FIG. 2).

In an aspect, predicted interval measurements (that is, time calipers or voltage calipers) may be utilized to update an EP map to assist with characterizing tissue, identifying the presence of a short pathway, identifying the location of a reentrant circuit, etc. For example, an element of the EP map may represent a caliper interval at a corresponding pacing location in the heart. In an aspect, an EP map may be color-coded to identify any of the foregoing.

Figure 14:
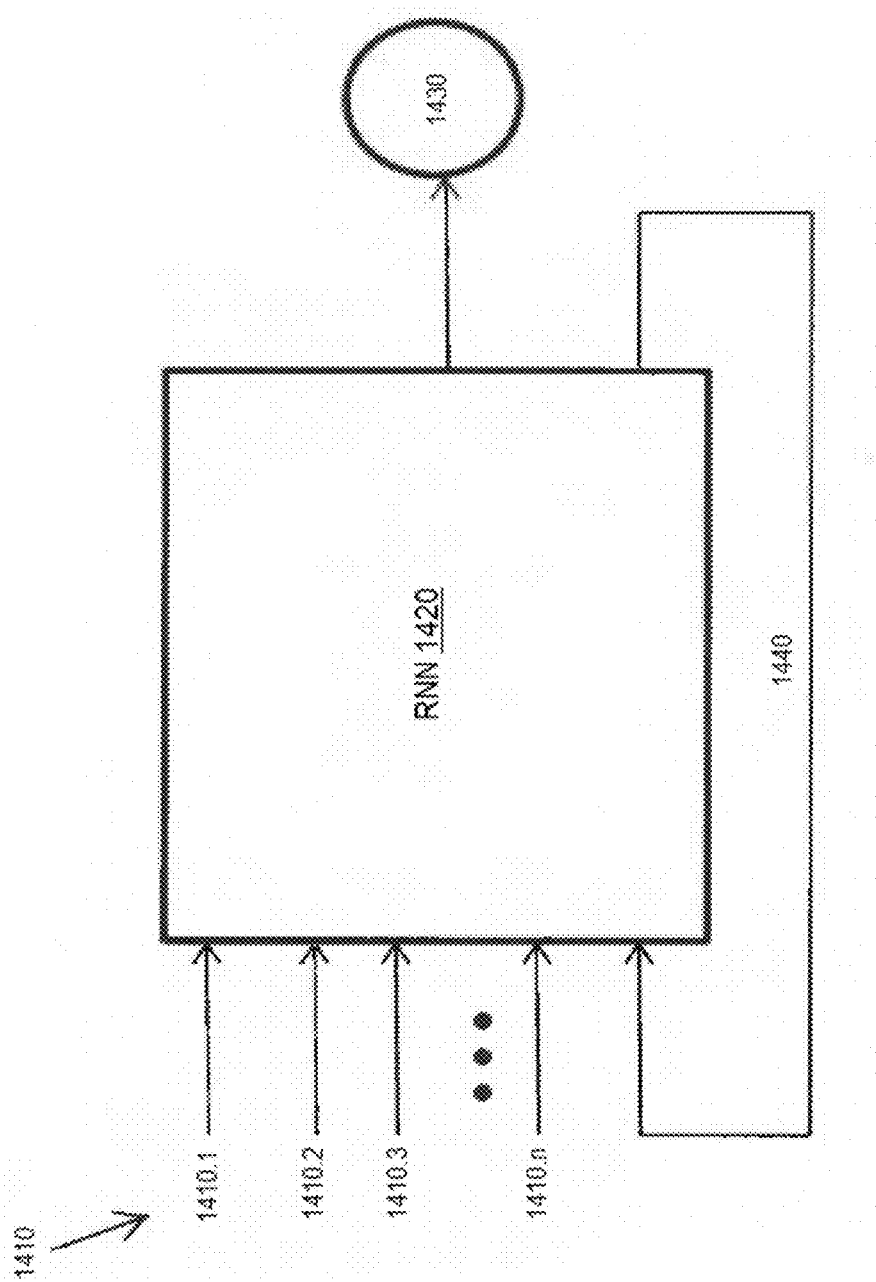
FIG. 14 is a functional block diagram of an example recurrent neural network (RNN), based on which one or more features of the disclosure may be implemented.

FIG. 14 illustrates a functional block diagram 1400 of an example RNN 1420, based on which one or more features of the disclosure may be implemented. Various machine learning models may be applied to implement the features described in reference to FIGS. 13A-B, such as those neural networks described with reference to FIGS. 4 and 14. For example, an RNN 1420 may be used. In an aspect, an RNN 1420 may receive paced pulses and native beats as input data 1410. The RNN 1420 is trained to produce, based on the input data 1410, an output 1430, such as interval measurement between the last paced pulse to the mapping annotation (i.e., native beat). The more input data 1410 received by the RNN 1420, the more accurate the output 1430 may be. The output of the RNN 1420, such as output 1430, may be used to train the RNN 1400, as illustrated by arrow 1440 in FIG. 14. Thus, if an output 1430 is accepted by a physician, the output 1430 may be used as an input 1410 to train the RNN 1420.

In an aspect, training and applying a machine learning model, as described in reference to FIGS. 12-14, may be performed by the systems described herein, 100 (FIG. 1) or 200 (FIG. 2), also representing a Mapping System, in real-time, on a server at the facility where the cardiac procedure is taking place, such as a hospital or medical facility, or at a remote location, such as in the cloud or at a training center.

Although features and elements are described above in particular combinations, one of ordinary skill in the art will appreciate that each feature or element can be used alone or in any combination with the other features and elements. In addition, although process steps are described above in a particular order, the steps can be performed in other desirable orders.

The methods, processes, modules, and systems described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, read only memory (ROM), random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

Further embodiments herein may be formed by supplementing an embodiment with one or more element from any one or more other embodiment herein, and/or substituting one or more element from one embodiment with one or more element from one or more other embodiment herein.

It is understood, therefore, that the disclosed subject matter is not limited to the particular embodiments disclosed, but is intended to cover all modifications which are within the spirit and scope of the disclosure as defined by the appended claims, the above description, and/or shown in the attached drawings.

What is claimed is:

1. A method for training a pacing maneuver prediction model, the method comprising:
   receiving a training dataset associated with a plurality of patients, for each patient among the plurality of patients the training dataset comprises:
      pacing maneuvers, each associated with pacing locations in a respective heart of the patient,
      corresponding interval measurements, each associated with a distance between a last paced pulse and a native beat from a corresponding pacing maneuver, and
      adjustments made by a physician during the pacing maneuvers; and
   performing the training of the pacing maneuver prediction model using the training data set, wherein the pacing maneuver prediction model predicts:
      preferences of the physician performing a pacing maneuver associated with a new patient that is not included in the plurality of the patients, wherein the preferences are learned based on the adjustments made by the physician during the pacing maneuvers included in the training data set, and
      an interval measurement based on the preferences and the pacing maneuver associated with the new patient.

2. The method of claim 1, further comprising, during a pacing maneuver procedure of the respective heart of the new patient:
   receiving a pacing maneuver associated with pacing locations in the respective heart of the new patient; and
   feeding the pacing maneuver prediction model with the received pacing maneuver to obtain a predicted interval measurement.

3. The method of claim 1, wherein:
   the training dataset further comprises, for each pacing maneuvers, a last paced pulse and a native beat detected from the pacing maneuver; and
   the pacing maneuver prediction model is further trained to detect a pacing pulse and a native beat from a received pacing maneuver.

4. The method of claim 1, wherein the interval measurement predicted is a time interval.

5. The method of claim 1, wherein the interval measurement predicted is a voltage interval.

6. The method of claim 1, wherein the training dataset is derived from electrocardiograms.

7. The method of claim 1, wherein the pacing maneuvers of the training dataset and the pacing maneuver associated with the new patient, each comprises a pacing sequence and a subsequent native beat.

8. A system for training a pacing maneuver prediction model, comprising:
   at least one processor; and
   memory storing instructions that, when executed by the at least one processor, cause the system to:
      receive a training dataset associated with a plurality of patients, for each patient among the plurality of patients the training dataset comprises:

pacing maneuvers, each associated with pacing locations in a respective heart of the patient, corresponding interval measurements, each associated with a distance between a last paced pulse and a native beat from a corresponding pacing maneuver, and adjustments made by a physician during the pacing maneuvers; and perform the training of the pacing maneuver prediction model using the training data set, wherein the pacing maneuver prediction model predicts:

preferences of the physician performing a pacing maneuver associated with a new patient that is not included in the plurality of the patients, wherein the preferences are learned based on the adjustments made by the physician during the pacing maneuvers included in the training data set, and an interval measurement based on the preferences and the pacing maneuver associated with the new patient.

9. A non-transitory computer-readable medium comprising instructions executable by at least one processor to perform a method for training a pacing maneuver prediction model, the method comprising:

receiving a training dataset associated with a plurality of patients, for each patient among the plurality of patients the training dataset comprises:

pacing maneuvers, each associated with pacing locations in a respective heart of the patient, corresponding interval measurements, each associated with a distance between a last paced pulse and a native beat from a corresponding pacing maneuver and adjustments made by a physician during the pacing maneuvers; and performing the training of the pacing maneuver prediction model using the training data set, wherein the pacing maneuver prediction model predicts:

preferences of the physician performing a pacing maneuver associated with a new patient that is not included in the plurality of the patient, wherein the preferences are learned based on the adjustments made by the physician during the pacing maneuvers included in the training data set, and an interval measurement based on the preferences and the pacing maneuver associated with the new patient.

10. A method of generating an electrophysiological (EP) cardiac map for the new patient, the method comprising:

training the pacing maneuver prediction model according to claim 2; and generating the EP cardiac map using the interval measurement predicted.

11. The system of claim 8, wherein during a pacing maneuver procedure of the respective heart of the new patient, the instructions further cause the system to:

receive a pacing maneuver associated with pacing locations in the respective heart of the new patient; and feed the pacing maneuver prediction model with the received pacing maneuver to obtain a predicted interval measurement.

12. The system of claim 11, wherein:

the training dataset further comprises, for each pacing maneuvers, a last paced pulse and a native beat detected from the pacing maneuver; and the pacing maneuver prediction model is further trained to detect a pacing pulse and a native beat from a received pacing maneuver.

13. The system of claim 8, wherein the interval measurement predicted is a time interval.

14. The system of claim 8, wherein the interval measurement predicted is a voltage interval.

15. The system of claim 8, wherein the training dataset is derived from electrocardiograms.

16. The system of claim 8, wherein the pacing maneuvers of the training dataset and the pacing maneuver associated with the new patient, each comprises a pacing sequence and a subsequent native beat.

17. The non-transitory computer-readable medium of claim 9, wherein during a pacing maneuver procedure of the respective heart of the new patient, the method further comprises:

receiving a pacing maneuver associated with pacing locations in the respective heart of the new patient; and feeding the pacing maneuver prediction model with the received pacing maneuver to obtain a predicted interval measurement.

18. The non-transitory computer-readable medium of claim 17, wherein:

the training dataset further comprises, for each pacing maneuvers, a last paced pulse and a native beat detected from the pacing maneuver; and the pacing maneuver prediction model is further trained to detect a pacing pulse and a native beat from a received pacing maneuver.

19. The non-transitory computer-readable medium of claim 9, wherein the interval measurement predicted is a time interval.

20. The non-transitory computer-readable medium of claim 9, wherein the interval measurement predicted is a voltage interval.

21. The non-transitory computer-readable medium of claim 9, wherein the training dataset is derived from electrocardiograms.

22. The non-transitory computer-readable medium of claim 9, wherein the pacing maneuvers of the training dataset and the pacing maneuver associated with the new patient, each comprises a pacing sequence and a subsequent native beat.

* * * * *